United States Patent
Riley et al.

(10) Patent No.: US 11,827,705 B2
(45) Date of Patent: Nov. 28, 2023

(54) METHODS TO PROTECT TRANSPLANTED TISSUE FROM REJECTION

(71) Applicant: THE TRUSTEES OF THE UNIVERSITY OF PENNSYLVANIA, Philadelphia, PA (US)

(72) Inventors: James L. Riley, Downingtown, PA (US); Gavin Ellis, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 173 days.

(21) Appl. No.: 15/936,524

(22) Filed: Mar. 27, 2018

(65) Prior Publication Data
US 2018/0282416 A1    Oct. 4, 2018

Related U.S. Application Data

(60) Provisional application No. 62/477,815, filed on Mar. 28, 2017.

(51) Int. Cl.
| | | |
|---|---|---|
| *C12N 15/85* | (2006.01) | |
| *C07K 16/28* | (2006.01) | |
| *C12N 5/0783* | (2010.01) | |
| *C07K 14/705* | (2006.01) | |
| *C07K 14/725* | (2006.01) | |
| *C12N 15/86* | (2006.01) | |
| *A61P 3/10* | (2006.01) | |
| *A61K 35/17* | (2015.01) | |
| *A61K 39/00* | (2006.01) | |

(52) U.S. Cl.
CPC .......... *C07K 16/2827* (2013.01); *A61K 35/17* (2013.01); *A61P 3/10* (2018.01); *C07K 14/7051* (2013.01); *C07K 14/70503* (2013.01); *C07K 14/70517* (2013.01); *C07K 14/70521* (2013.01); *C07K 16/2833* (2013.01); *C12N 5/0637* (2013.01); *C12N 15/86* (2013.01); *A61K 2039/5156* (2013.01); *C07K 2317/56* (2013.01); *C07K 2317/622* (2013.01); *C07K 2317/74* (2013.01); *C07K 2319/02* (2013.01); *C07K 2319/03* (2013.01); *C07K 2319/33* (2013.01); *C12N 2510/00* (2013.01); *C12N 2740/15043* (2013.01); *C12N 2830/00* (2013.01)

(58) Field of Classification Search
None
See application file for complete search history.

(56) References Cited

U.S. PATENT DOCUMENTS

| | | |
|---|---|---|
| 5,350,674 A | 9/1994 | Boenisch et al. |
| 5,565,332 A | 10/1996 | Hoogenboom et al. |
| 5,573,905 A | 11/1996 | Lerner et al. |
| 5,585,362 A | 12/1996 | Wilson et al. |
| 5,994,136 A | 11/1999 | Naldini et al. |
| 6,013,516 A | 1/2000 | Verma et al. |
| 7,754,482 B2 | 7/2010 | Riley et al. |
| 8,722,400 B2 | 5/2014 | Riley et al. |
| 9,555,105 B2 | 1/2017 | Riley et al. |
| 2013/0101567 A1 | 4/2013 | Riley et al. |
| 2014/0328812 A1* | 11/2014 | Campana ........... C07K 16/2866 424/93.21 |
| 2015/0051266 A1 | 2/2015 | Kochenderfer |
| 2015/0079093 A1* | 3/2015 | Stuhler .................. A61P 19/02 536/23.53 |
| 2018/0111993 A1 | 4/2018 | Pulé |
| 2020/0283529 A1 | 9/2020 | Levings |

FOREIGN PATENT DOCUMENTS

| | | |
|---|---|---|
| EP | 3134095 | 3/2017 |
| WO | 2010132532 | 11/2010 |
| WO | 2013104804 A2 | 7/2013 |
| WO | 2016160622 | 10/2016 |
| WO | 2019056106 A1 | 3/2019 |

OTHER PUBLICATIONS

Spooner et al, Cell Biophys, 22(1-3): 225-42, 1993). (Year: 1993).*
PCT/US2018/024519 International Search Report and Written Opinion dated Jun. 25, 2018.
Boardman, et al., "Expression of a Chimeric Antigen Receptor Specific for Donor HLA Class I Enhances the Potency of Human Regulatory T Cells in Preventing Human Skin Transplant Rejection.", Am J Transplant. Apr. 2017;17(4):931-943. doi: 10.1111/ajt.14185. Epub Feb. 1, 2017.
Bruggermann, et al., "Designer Mice: The Production of Human Antibody Repertoires in Transgenic Animals.", Year in Immunol., 7:33-40 (1993).
Clackson, et al., "Making antibody fragments using phage display libraries", Nature, 352:624-628 (1991) (abstract).
Danthinne, et al., "Production of first generation adenovirus vectors: a review.", Gene Therapy (2000) 7(20): 1707-1714.
Davison, et al., "The Human HLA-A*0201 Allele, Expressed in Hamster Cells, Is Not a High-Affinity Receptor for Adenovirus Type 5 Fiber", Journal of Virology, 73(5):4513-4517 May 1999.
Duchosal, et al., "Immunization of hu-PBL-SCID mice and the rescue of human monoclonal Fab fragments through combinatorial libraries", Nature, 355:258-262 (1992).
Edinger, "Driving allotolerance: CAR-expressing Tregs for tolerance induction in organ and stem cell transplantation.", 2016, J Clin Invest 126(4):1248-50 (Apr. 1, 2016).
Gillis, et al., "Contribution of human FcγRs to disease with evidence from human polymorphisms and transgenic animal studies", Front Immunol. May 30, 2014;5:254.
Glaser, et al., "Novel antibody hinge regions for efficient production of CH2 domain-deleted antibodies.", J. Biol. Chem. (2005) 280:41494-41503.

(Continued)

*Primary Examiner* — Marcia S Noble
(74) *Attorney, Agent, or Firm* — Saul Ewing LLP; Kathryn Doyle

(57) ABSTRACT

The present invention includes compositions and methods for an HLA-A2 specific chimeric antigen receptor (CAR). In certain embodiments the HLA-A2 specific CAR is expressed on a T regulatory cell. In certain embodiments, the HLA-A2 specific CAR protects transplanted tissue from rejection.

13 Claims, 5 Drawing Sheets

Specification includes a Sequence Listing.

(56) References Cited

OTHER PUBLICATIONS

Griffith, et al., "Human anti-self antibodies with high specificity from phage display libraries", EMBO J., 12:725-734 (1993).
Hoogenboom, et al., "By-passing immunisation. Human antibodies from synthetic repertoires of germline VH gene segments arranged in vitro.", J Mol Biol Sep. 20, 1992;227(2):381-8. (Abstract).
Huck, et al., "Sequence of a human immunoglobulin gamma 3 heavy chain constant region gene: comparison with the other human C gamma genes.", Nucleic Acids Res. Feb. 25, 1986; 14(4): 1779-1789.
Hudecek, et al., "The non-signaling extracellular spacer domain of chimeric antigen receptors is decisive for in vivo antitumor activity", Cancer Immunol Res. 3(2), 2015, 125-135.
Huston, et al., "Protein engineering of antibody binding sites: Recovery of sepcific activity in an anti-digoxin single-chain Fv analogue produced in *Escherichia coli*.", 1988, Proc Natl Acad Sci USA 85:5879-5883.
Inaguma, et al., "Construction and molecular characterization of a T-cell receptor-like antibody and CAR-T cells specific for minor histocompatibility antigen HA-1H", Gene Therapy (2014) 21, 575-584.
Jakobovits, et al., "Analysis of homozygous mutant chimeric mice: Deletion of the immunoglobulin heavy-chain joining region blocks B-cell development and antibody production", Proc. Natl. Acad. Sci. 90, 1993, 2551-2555.
Jakobovits, et al., "Germ-line transmission and expression of a human-derived yeast artificial chromosome", Nature, 362:255-258 (1993).
Johnson, et al., "Human antibody engineering", Current Opinion in Structural Biology 3:564-571 (1993).
Jones, et al., "Replacing the complementarity-determining regions in a human antibody with those from a mouse", Nature, 321:522-525 (1986).
Klar, et al., "Treatment with 5-Aza-2'-Deoxycytidine Induces Expression of NY-ESO-1 and Facilitates Cytotoxic T Lymphocyte-Mediated Tumor Cell Killing.", Plos One | DOI:10.1371/journal.pone.0139221 Oct. 8, 2015.
Lamers, et al., "T Cell Receptor-Engineered T Cells to Treat Solid Tumors: T Cell Processing Toward Optimal T Cell Fitness", Human Gene Therapy Methods 25:345-357 (Dec. 2014).
Liu, et al., "Targeting Alpha-Fetoprotein (AFP)-MHC Complex with CAR T-Cell Therapy for Liver Cancer.", Clin Cancer Res. Jan. 15, 2017;23(2):478-488.
Lonberg, et al., "Human antibodies from transgenic mice.", Int. Rev. Immunol., 13:65-93 (1995).
Ma, et al., "A novel TCR-like CAR with specificity for PR1/HLA-A2 effectively targets myeloid leukemia in vitro when expressed in human adult peripheral blood and cord blood T cells.", Cytotherapy. Aug. 2016;18(8):985-94.
MacDonald, et al., "Alloantigen-specific regulatory T cells generated with a chimeric antigen receptor.", J Clin Invest. 2016; 126(4):1413-1424.
Marks, et al., "By-passing immunization. Human antibodies from V-gene libraries displayed on phage", J. Mol. Biol. 222:581-597 (1991).
McCafferty, et al., "Phage antibodies: filamentous phage displaying antibody variable domains", Nature, 348:552-553 (1990)93).
McDonald, et al., "Coxackie and adenovirus receptor (CAR)-dependent and major histocompatibility complex (MHC) class I-independent uptake of recombinant adenoviruses into human tumour cells.", Gene Therapy (1999) 6 (9):1512-1519.
Noyan, et al., "Prevention of Allograft Rejection by Use of Regulatory T Cells With an MHC-Specific Chimeric Antigen Receptor.", Am J Transplant. Apr. 2017;17(4):917-930.
Oren, et al., "Functional Comparison of Engineered T Cells Carrying a Native TCR versus TCR-like Antibody-based Chimeric Antigen Rectptors Indicates Affinity/Avidity Thresholds.", J Immunol 2014; 193:5733-5743; Prepublished online Oct. 31, 2014.
Park, et al., "Are All Chimeric Antigen Receptors Created Equal?", J Clin Oncol. Feb. 20, 2015,33(6):651-3.
Presta, "Antibody engineering.", Current Opinion in Structural Biology, vol. 2, Issue 4, Aug. 1992, pp. 593-596 (Abstract).
Reichmann, et al., "Reshaping Human Antibodies for Therapy", Nature. 332(6162), 1988, 323-327.
Roder, et al., "The EBV-hybridoma technique", Methods Enzymol., 121:140-167 (1986).
Rosenberg, et al., "Use of Tumor-Infiltrating Lymphocytes and Interleukin-2 in the Immunotherapy of Patients with Metastatic Melanoma", New Eng. J. of Med. 319:1676-1680, 1988.
Shen, et al., "Engineering Peptide Linkers for scFv Immunosensors", Anal Chem. Mar. 15, 2008; 80(6): 1910-1917.
Tan, et al., "Influence of the hinge region on complement activation, C1q binding, and segmental flexibility in chimeric human immunoglobulins.", Proc Natl Acad Sci U S A. Jan. 1990; 87(1): 162-166.
Tassev, et al., "Retargeting NK92 cells using an HLA-A2-restricted, EBNA3C-specific chimeric antigen receptor.", Cancer Gene Therapy (2012) 19, 84-100.
Vaughan, et al., "Human antibodies with sub-nanomolar affinities isolated from a large non-immunized phage display library.", Vaughan et al., 1996, Nature Biotech., 14:309-14 (Abstract).
Watkins, et al., "The isolation and characterisation of human monoclonal HLA-A2 antibodies from an immune V gene phage display library.", Tissue Antigens. Mar. 2000;55(3):219-28. (Abstract).
Yan, et al., "Engineering Upper Hinge Improves Stability and Effector Function of a Human IgG1.", J Biol Chem. Feb. 17, 2012;287(8):5891-7.
Zhang, et al., "Anti-melanoma activity of T cells redirected with a TCR-like chimeric antigen receptor.", Sci Rep. Jan. 6, 2014;4:3571. doi: 10.1038/srep03571.
Zhao, et al., "Multiple injections of electroporated autologous T cells expressing a chimeric antigen receptor mediate regression of human disseminated tumor", Cancer Res. Nov. 15, 2010; 70(22): 9053-9061.
Zhou, et al., "CD123 redirected multiple virus-specific T cells for acute myeloid leukemia.", Leuk Res. Feb. 2016;41:76-84. doi: 10.1016/j.leukres.2015.12.003. Epub Dec. 19, 2015. (Abstract).
David L. Hermanson et al, "Utilizing Chimeric Antigen Receptors to Direct Natural Killer Cell Activity", Frontiers in Immunology, (Apr. 28, 2015), vol. 6, doi:10.3389/fimmu.2015.00195, XP055333119.
O'Hear, et al., "Anti-CD33 chimeric antigen receptor targeting of acute myeloid leukemia.", 2014, Hematologica 100 (3):336-344.
EP125553 Extended European Search Report and European Search Opinion dated Nov. 17, 2020.
Ping Y., et al., "Augmenting the Effectiveness of CAR-T Cells by Enhanced Self-Delivery of PD-1-Neutralizing scFv," Front. Cell Dev. Biol., 8:803, pages (Aug. 18, 2020).
Singh, N., et al., "Antigen-independent activation enhances the efficacy of 41BB co-stimulated CD22 CAR T cells," Nat Med., Author manuscript, available in PMCID: PMC8451032, pp. 1-27, Sep. 20, 2021; Published in final edited form as: Nat Med. May 2021; 27(5): 842-850, published online Apr. 22, 2021. doi: 10.1038/s41591-021-01326-5.
Watkins, N.A., et al., "The isolation and characterisation of human monoclonal HLA-A2 antibodies from an immune V gene phage display library", Tissue Antigens, Mar. 2000, 55(3):219-228.

\* cited by examiner

SEQUENCE LISTING

```
<160> NUMBER OF SEQ ID NOS: 48

<210> SEQ ID NO 1
<211> LENGTH: 245
<212> TYPE: PRT
<213> ORGANISM: Artificial sequence
<220> FEATURE:
<223> OTHER INFORMATION: HLA-A2 scFv

<400> SEQUENCE: 1

Gln Val Gln Leu Val Gln Ser Gly Gly Gly Val Val Gln Pro Gly Gly
1               5                   10                  15

Ser Leu Arg Val Ser Cys Ala Ala Ser Gly Val Thr Leu Ser Asp Tyr
            20                  25                  30

Gly Met His Trp Val Arg Gln Ala Pro Gly Lys Gly Leu Glu Trp Met
        35                  40                  45

Ala Phe Ile Arg Asn Asp Gly Ser Asp Lys Tyr Tyr Ala Asp Ser Val
    50                  55                  60

Lys Gly Arg Phe Thr Ile Ser Arg Asp Asn Ser Lys Lys Thr Val Ser
65                  70                  75                  80

Leu Gln Met Ser Ser Leu Arg Ala Glu Asp Thr Ala Val Tyr Tyr Cys
                85                  90                  95

Ala Lys Asn Gly Glu Ser Gly Pro Leu Asp Tyr Trp Tyr Phe Asp Leu
            100                 105                 110

Trp Gly Arg Gly Thr Leu Val Thr Val Ser Gly Gly Gly Gly Ser Gly
        115                 120                 125

Gly Gly Gly Ser Gly Gly Gly Ser Asp Val Val Met Thr Gln Ser
    130                 135                 140

Pro Ser Ser Leu Ser Ala Ser Val Gly Asp Arg Val Thr Ile Thr Cys
145                 150                 155                 160

Gln Ala Ser Gln Asp Ile Ser Asn Tyr Leu Asn Trp Tyr Gln Gln Lys
                165                 170                 175

Pro Gly Lys Ala Pro Lys Leu Leu Ile Tyr Asp Ala Ser Asn Leu Glu
            180                 185                 190

Thr Gly Val Pro Ser Arg Phe Ser Gly Ser Gly Ser Gly Thr Asp Phe
        195                 200                 205

Thr Phe Thr Ile Ser Ser Leu Gln Pro Glu Asp Phe Ala Thr Tyr Tyr
    210                 215                 220

Cys Gln Gln Tyr Ser Ser Phe Pro Leu Thr Phe Gly Gly Gly Thr Lys
225                 230                 235                 240

Val Asp Ile Lys Arg
                245
```

<210> SEQ ID NO 2
<211> LENGTH: 735
<212> TYPE: DNA
<213> ORGANISM: Artificial sequence
<220> FEATURE:
<223> OTHER INFORMATION: HLA-A2 scFv

<400> SEQUENCE: 2

```
caggtgcagc tggtgcagtc tgggggaggc gtggtccagc ctggggggtc cctgagagtc    60
tcctgtgcag cgtctggggt caccctcagt gattatggca tgcattgggt ccgccaggct   120
ccaggcaagg gctggagtg  gatggcttt  atacggaatg atggaagtga taaatattat   180
gcagactccg tgaagggccg attcaccatc tccagagaca actccaagaa aacagtgtct   240
ctgcaaatga gcagtctcag agctgaagac acggctgtgt attactgtgc gaaaaatggc   300
gaatctgggc cttttggacta ctggtacttc gatctctggg gccgtggcac cctggtcacc   360
gtgtcgggtg gcgtggctc  gggcggtggt gggtcgggtg gcggcggatc tgatgttgtg   420
atgactcagt ctccatcctc cctgtctgca tctgtaggag acagagtcac catcacttgc   480
caggcgagtc aggacattag caactattta aattggtatc agcagaaacc agggaaagcc   540
cctaagctcc tgatctacga tgcatccaat ttggaaacag gggtcccatc aaggttcagt   600
ggaagtggat ctgggacaga ttttactttc accatcagca gcctgcagcc tgaggatttt   660
gcaacttatt actgccaaca atatagtagt tttccgctca ctttcggcgg agggaccaaa   720
gtggatatca aacgt                                                    735
```

<210> SEQ ID NO 3
<211> LENGTH: 117
<212> TYPE: PRT
<213> ORGANISM: Artificial sequence
<220> FEATURE:
<223> OTHER INFORMATION: HLA-A2 scFv heavy chain (HC) variable region

<400> SEQUENCE: 3

```
Gln Val Gln Leu Val Gln Ser Gly Gly Gly Val Val Gln Pro Gly Gly
1               5                   10                  15

Ser Leu Arg Val Ser Cys Ala Ala Ser Gly Val Thr Leu Ser Asp Tyr
            20                  25                  30

Gly Met His Trp Val Arg Gln Ala Pro Gly Lys Gly Leu Glu Trp Met
        35                  40                  45

Ala Phe Ile Arg Asn Asp Gly Ser Asp Lys Tyr Tyr Ala Asp Ser Val
    50                  55                  60

Lys Gly Arg Phe Thr Ile Ser Arg Asp Asn Ser Lys Lys Thr Val Ser
65                  70                  75                  80

Leu Gln Met Ser Ser Leu Arg Ala Glu Asp Thr Ala Val Tyr Tyr Cys
                85                  90                  95

Ala Lys Asn Gly Glu Ser Gly Pro Leu Asp Tyr Trp Tyr Phe Asp Leu
            100                 105                 110

Trp Gly Arg Gly Thr
        115
```

<210> SEQ ID NO 4
<211> LENGTH: 351
<212> TYPE: DNA
<213> ORGANISM: Artificial sequence
<220> FEATURE:
<223> OTHER INFORMATION: HLA-A2 scFv heavy chain (HC) variable region

<400> SEQUENCE: 4

```
caggtgcagc tggtgcagtc tgggggaggc gtggtccagc ctgggggtc cctgagagtc     60
tcctgtgcag cgtctggggt caccctcagt gattatggca tgcattgggt ccgccaggct   120
ccagcaagg gctggagtg gatggctttt atacggaatg atggaagtga taaatattat    180
gcagactccg tgaagggccg attcaccatc tccagagaca actccaagaa aacagtgtct   240
ctgcaaatga gcagtctcag agctgaagac acggctgtgt attactgtgc gaaaaatggc   300
gaatctgggc ctttggacta ctggtacttc gatctctggg gccgtggcac c            351
```

<210> SEQ ID NO 5
<211> LENGTH: 5
<212> TYPE: PRT
<213> ORGANISM: Artificial sequence
<220> FEATURE:
<223> OTHER INFORMATION: HLA-A2 scFv HC CDR1

<400> SEQUENCE: 5

Asp Tyr Gly Met His
1               5

<210> SEQ ID NO 6
<211> LENGTH: 17
<212> TYPE: PRT
<213> ORGANISM: Artificial sequence
<220> FEATURE:
<223> OTHER INFORMATION: HLA-A2 scFv HC CDR2

<400> SEQUENCE: 6

Phe Ile Arg Asn Asp Gly Ser Asp Lys Tyr Tyr Ala Asp Ser Val Lys
1               5                   10                  15

Gly

<210> SEQ ID NO 7
<211> LENGTH: 14
<212> TYPE: PRT
<213> ORGANISM: Artificial sequence
<220> FEATURE:
<223> OTHER INFORMATION: HLA-A2 scFv HC CDR3

<400> SEQUENCE: 7

Asn Gly Glu Ser Gly Pro Leu Asp Tyr Trp Tyr Phe Asp Leu
1               5                   10

<210> SEQ ID NO 8
<211> LENGTH: 108
<212> TYPE: PRT
<213> ORGANISM: Artificial sequence
<220> FEATURE:
<223> OTHER INFORMATION: HLA-A2 scFv light chain (LC) variable region

<400> SEQUENCE: 8

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln Tyr Ser Ser Phe Pro Leu
                85                  90                  95

Thr Phe Gly Gly Gly Thr Lys Val Asp Ile Lys Arg
            100                 105

<210> SEQ ID NO 9
<211> LENGTH: 324
<212> TYPE: DNA
<213> ORGANISM: Artificial sequence
<220> FEATURE:
<223> OTHER INFORMATION: HLA-A2 scFv LC variable region

<400> SEQUENCE: 9
gatgttgtga tgactcagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg gaagtggatc tgggacagat tttactttca ccatcagcag cctgcagcct     240
gaggattttg caacttatta ctgccaacaa tatagtagtt ttccgctcac tttcggcgga     300
gggaccaaag tggatatcaa acgt                                            324

<210> SEQ ID NO 10
<211> LENGTH: 11
<212> TYPE: PRT
<213> ORGANISM: Artificial sequence
<220> FEATURE:
<223> OTHER INFORMATION: HLA-A2 scFv LC CDR1

<400> SEQUENCE: 10

Gln Ala Ser Gln Asp Ile Ser Asn Tyr Leu Asn
1               5                   10

<210> SEQ ID NO 11
<211> LENGTH: 7
<212> TYPE: PRT
<213> ORGANISM: Artificial sequence
<220> FEATURE:
<223> OTHER INFORMATION: HLA-A2 scFv LC CDR2

<400> SEQUENCE: 11

Asp Ala Ser Asn Leu Glu Thr
1               5

<210> SEQ ID NO 12
<211> LENGTH: 9
<212> TYPE: PRT
<213> ORGANISM: Artificial sequence
<220> FEATURE:
<223> OTHER INFORMATION: HLA-A2 scFv LC CDR3

<400> SEQUENCE: 12

Gln Gln Tyr Ser Ser Phe Pro Leu Thr
1               5

<210> SEQ ID NO 13
<211> LENGTH: 21
<212> TYPE: PRT
<213> ORGANISM: Artificial sequence
<220> FEATURE:
<223> OTHER INFORMATION: CD8 signal peptide

<400> SEQUENCE: 13

Met Ala Leu Pro Val Thr Ala Leu Leu Leu Pro Leu Ala Leu Leu Leu
1               5                   10                  15

His Ala Ala Arg Pro
            20

<210> SEQ ID NO 14
<211> LENGTH: 63
<212> TYPE: DNA
<213> ORGANISM: Artificial sequence
<220> FEATURE:
<223> OTHER INFORMATION: CD8 signal peptide

<400> SEQUENCE: 14
atggccttac cagtgaccgc cttgctcctg ccgctggcct tgctgctcca cgccgccagg    60
ccg                                                                  63

<210> SEQ ID NO 15
<211> LENGTH: 45
<212> TYPE: PRT
<213> ORGANISM: Artificial sequence
<220> FEATURE:
<223> OTHER INFORMATION: CD8 hinge

<400> SEQUENCE: 15

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 16
<211> LENGTH: 135
<212> TYPE: DNA
<213> ORGANISM: Artificial sequence
<220> FEATURE:
<223> OTHER INFORMATION: CD8 hinge

<400> SEQUENCE: 16
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                    135

<210> SEQ ID NO 17
<211> LENGTH: 27
<212> TYPE: PRT
<213> ORGANISM: Artificial sequence
<220> FEATURE:
<223> OTHER INFORMATION: CD28 transmembrane domain

<400> SEQUENCE: 17

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 18
<211> LENGTH: 81
<212> TYPE: DNA
<213> ORGANISM: Artificial sequence
<220> FEATURE:
<223> OTHER INFORMATION: CD28 transmembrane domain

<400> SEQUENCE: 18
ttttgggtgc tggtggtggt tggtggagtc ctggcttgct atagcttgct agtaacagtg    60
gcctttatta ttttctgggt g    81

<210> SEQ ID NO 19
<211> LENGTH: 41
<212> TYPE: PRT
<213> ORGANISM: Artificial sequence
<220> FEATURE:
<223> OTHER INFORMATION: CD28 intracellular domain

<400> SEQUENCE: 19

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 20
<211> LENGTH: 123
<212> TYPE: DNA
<213> ORGANISM: Artificial sequence
<220> FEATURE:
<223> OTHER INFORMATION: CD28 intracellular domain

<400> SEQUENCE: 20
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc   123

<210> SEQ ID NO 21
<211> LENGTH: 112
<212> TYPE: PRT
<213> ORGANISM: Artificial sequence
<220> FEATURE:
<223> OTHER INFORMATION: CD3 zeta domain

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

-continued

```
<210> SEQ ID NO 22
<211> LENGTH: 336
<212> TYPE: DNA
<213> ORGANISM: Artificial sequence
<220> FEATURE:
<223> OTHER INFORMATION: CD3 zeta domain

<400> SEQUENCE: 22
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240 cggagggggca aggggcacga tggcctttac cagggtctca gtacagccac caaggacacc     300
tacgacgccc ttcacatgca ggccctgccc cctcgc                               336

<210> SEQ ID NO 23
<211> LENGTH: 497
<212> TYPE: PRT
<213> ORGANISM: Artificial sequence
<220> FEATURE:
<223> OTHER INFORMATION: HLA-A2 CAR

<400> SEQUENCE: 23
```

Met Ala Leu Pro Val Thr Ala Leu Leu Leu Pro Leu Ala Leu Leu Leu
1               5                   10                  15

His Ala Ala Arg Pro Gly Ser Gln Val Gln Leu Val Gln Ser Gly Gly
                20                  25                  30

Gly Val Val Gln Pro Gly Gly Ser Leu Arg Val Ser Cys Ala Ala Ser
            35                  40                  45

Gly Val Thr Leu Ser Asp Tyr Gly Met His Trp Val Arg Gln Ala Pro
        50                  55                  60

Gly Lys Gly Leu Glu Trp Met Ala Phe Ile Arg Asn Asp Gly Ser Asp
65                  70                  75                  80

Lys Tyr Tyr Ala Asp Ser Val Lys Gly Arg Phe Thr Ile Ser Arg Asp
                85                  90                  95

Asn Ser Lys Lys Thr Val Ser Leu Gln Met Ser Ser Leu Arg Ala Glu
            100                 105                 110

Asp Thr Ala Val Tyr Tyr Cys Ala Lys Asn Gly Glu Ser Gly Pro Leu
        115                 120                 125

Asp Tyr Trp Tyr Phe Asp Leu Trp Gly Arg Gly Thr Leu Val Thr Val
    130                 135                 140

Ser Gly Gly Gly Gly Ser Gly Gly Gly Ser Gly Gly Gly Gly Ser
145                 150                 155                 160

Asp Val Val Met Thr Gln Ser Pro Ser Ser Leu Ser Ala Ser Val Gly
                165                 170                 175

Asp Arg Val Thr Ile Thr Cys Gln Ala Ser Gln Asp Ile Ser Asn Tyr
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Phe Ala Thr Tyr Tyr Cys Gln Gln Tyr Ser Ser Phe Pro Leu
                245                 250                 255

```
Thr Phe Gly Gly Gly Thr Lys Val Asp Ile Lys Arg Ser Gly Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Phe Trp Val Leu Val
305                 310                 315                 320

Val Val Gly Gly Val Leu Ala Cys Tyr Ser Leu Leu Val Thr Val Ala
                325                 330                 335

Phe Ile Ile Phe Trp Val Arg Ser Lys Arg Ser Arg Leu Leu His Ser
            340                 345                 350

Asp Tyr Met Asn Met Thr Pro Arg Arg Pro Gly Pro Thr Arg Lys His
        355                 360                 365

Tyr Gln Pro Tyr Ala Pro Pro Arg Asp Phe Ala Ala Tyr Arg Ser Ile
    370                 375                 380

Asp Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 24
<211> LENGTH: 1491
<212> TYPE: DNA
<213> ORGANISM: Artificial sequence
<220> FEATURE:
<223> OTHER INFORMATION: HLA-A2 CAR

<400> SEQUENCE: 24
atggccttac cagtgaccgc cttgctcctg ccgctggcct tgctgctcca cgccgccagg      60
ccgggatccc aggtgcagct ggtgcagtct gggggaggcg tggtccagcc tgggggtcc     120 ctgagagtct cctgtgcagc gtctggggtc accctcagtg attatggcat gcattgggtc     180
cgccaggctc caggcaaggg gctggagtgg atggctttta tacggaatga tggaagtgat     240
aaatattatg cagactccgt gaagggccga ttcaccatct ccagagacaa ctccaagaaa     300
acagtgtctc tgcaaatgag cagtctcaga gctgaagaca cggctgtgta ttactgtgcg     360
aaaaatggcg aatctgggcc tttgactac tggtacttcg atctctgggg ccgtggcacc     420
ctggtcaccg tgtcgggtgg cggtggctcg ggcggtggtg ggtcgggtgg cggcggatct     480
gatgttgtga tgactcagtc tccatcctcc ctgtctgcat ctgtaggaga cagagtcacc     540
atcacttgcc aggcgagtca ggacattagc aactatttaa attggtatca gcagaaacca     600
gggaaagccc ctaagctcct gatctacgat gcatccaatt tggaaacagg ggtcccatca     660
```

-continued

```
aggttcagtg gaagtggatc tgggacagat tttactttca ccatcagcag cctgcagcct    720
gaggattttg caacttatta ctgccaacaa tatagtagtt ttccgctcac tttcggcgga    780
gggaccaaag tggatatcaa acgttccgga accacgacgc cagcgccgcg accaccaaca    840
ccggcgccca ccatcgcgtc gcagcccctg tccctgcgcc cagaggcgtg ccggccagcg    900
gcggggggcg cagtgcacac gaggggggctg gacttcgcct gtgattttttg ggtgctggtg    960 gtggttggtg gagtcctggc ttgctatagc ttgctagtaa cagtggcctt tattattttc   1020
tgggtgagga gtaagaggag caggctcctg cacagtgact acatgaacat gactccccgc   1080
cgccccgggc ccacccgcaa gcattaccag ccctatgccc caccacgcga cttcgcagcc   1140
tatcgctcca tcgatagagt gaagttcagc aggagcgcag acgccccgc gtaccagcag   1200 ggccagaacc agctctataa cgagctcaat ctaggacgaa gagaggagta cgatgttttg   1260
gacaagagac gtggccggga ccctgagatg gggggaaagc cgagaaggaa gaaccctcag   1320
gaaggcctgt acaatgaact gcagaaagat aagatggcgg aggcctacag tgagattggg   1380
atgaaaggcg agcgccggag gggcaagggg cacgatggcc tttaccaggg tctcagtaca   1440
gccaccaagg acacctacga cgcccttcac atgcaggccc tgccccctcg c           1491
```

<210> SEQ ID NO 25
<211> LENGTH: 5
<212> TYPE: PRT
<213> ORGANISM: Artificial sequence
<220> FEATURE:
<223> OTHER INFORMATION: linker
<220> FEATURE:
<221> NAME/KEY: REPEAT
<222> LOCATION: (1)..(5)
<223> OTHER INFORMATION: Repeat n times. n is an integer of at least 1.

<400> SEQUENCE: 25

Gly Ser Gly Gly Ser
1               5

<210> SEQ ID NO 26
<211> LENGTH: 4
<212> TYPE: PRT
<213> ORGANISM: Artificial sequence
<220> FEATURE:
<223> OTHER INFORMATION: linker
<220> FEATURE:
<221> NAME/KEY: REPEAT
<222> LOCATION: (1)..(4)
<223> OTHER INFORMATION: Repeat n times. n is an integer of at least 1.

<400> SEQUENCE: 26

Gly Gly Gly Ser
1

<210> SEQ ID NO 27
<211> LENGTH: 5
<212> TYPE: PRT
<213> ORGANISM: Artificial sequence
<220> FEATURE:
<223> OTHER INFORMATION: linker
<220> FEATURE:
<221> NAME/KEY: REPEAT
<222> LOCATION: (1)..(5)
<223> OTHER INFORMATION: Repeat n times. n is an integer of at least 1.

<400> SEQUENCE: 27

Gly Gly Gly Gly Ser
1               5

```
<210> SEQ ID NO 28
<211> LENGTH: 4
<212> TYPE: PRT
<213> ORGANISM: Artificial sequence
<220> FEATURE:
<223> OTHER INFORMATION: linker

<400> SEQUENCE: 28

Gly Gly Ser Gly
1

<210> SEQ ID NO 29
<211> LENGTH: 5
<212> TYPE: PRT
<213> ORGANISM: Artificial sequence
<220> FEATURE:
<223> OTHER INFORMATION: linker

<400> SEQUENCE: 29

Gly Gly Ser Gly Gly
1               5

<210> SEQ ID NO 30
<211> LENGTH: 5
<212> TYPE: PRT
<213> ORGANISM: Artificial sequence
<220> FEATURE:
<223> OTHER INFORMATION: linker

<400> SEQUENCE: 30

Gly Ser Gly Ser Gly
1               5

<210> SEQ ID NO 31
<211> LENGTH: 5
<212> TYPE: PRT
<213> ORGANISM: Artificial sequence
<220> FEATURE:
<223> OTHER INFORMATION: linker

<400> SEQUENCE: 31

Gly Ser Gly Gly Gly
1               5

<210> SEQ ID NO 32
<211> LENGTH: 5
<212> TYPE: PRT
<213> ORGANISM: Artificial sequence
<220> FEATURE:
<223> OTHER INFORMATION: linker

<400> SEQUENCE: 32

Gly Gly Gly Ser Gly
1               5

<210> SEQ ID NO 33
<211> LENGTH: 5
<212> TYPE: PRT
<213> ORGANISM: Artificial sequence
<220> FEATURE:
<223> OTHER INFORMATION: linker

<400> SEQUENCE: 33

Gly Ser Ser Ser Gly
1               5
```

<210> SEQ ID NO 34
<211> LENGTH: 5
<212> TYPE: PRT
<213> ORGANISM: Artificial sequence
<220> FEATURE:
<223> OTHER INFORMATION: linker

<400> SEQUENCE: 34

Gly Gly Gly Gly Ser
1               5

<210> SEQ ID NO 35
<211> LENGTH: 15
<212> TYPE: PRT
<213> ORGANISM: Artificial sequence
<220> FEATURE:
<223> OTHER INFORMATION: linker

<400> SEQUENCE: 35

Gly Gly Gly Gly Ser Gly Gly Gly Gly Ser Gly Gly Gly Gly Ser
1               5                   10                  15

<210> SEQ ID NO 36
<211> LENGTH: 45
<212> TYPE: DNA
<213> ORGANISM: Artificial sequence
<220> FEATURE:
<223> OTHER INFORMATION: linker

<400> SEQUENCE: 36
ggtggcggtg gctcgggcgg tggtgggtcg ggtggcggcg gatct            45

<210> SEQ ID NO 37
<211> LENGTH: 5
<212> TYPE: PRT
<213> ORGANISM: Artificial sequence
<220> FEATURE:
<223> OTHER INFORMATION: hinge

<400> SEQUENCE: 37

Asp Lys Thr His Thr
1               5

<210> SEQ ID NO 38
<211> LENGTH: 4
<212> TYPE: PRT
<213> ORGANISM: Artificial sequence
<220> FEATURE:
<223> OTHER INFORMATION: hinge

<400> SEQUENCE: 38

Cys Pro Pro Cys
1

<210> SEQ ID NO 39
<211> LENGTH: 15
<212> TYPE: PRT
<213> ORGANISM: Artificial sequence
<220> FEATURE:
<223> OTHER INFORMATION: hinge

<400> SEQUENCE: 39

Cys Pro Glu Pro Lys Ser Cys Asp Thr Pro Pro Pro Cys Pro Arg
1               5                   10                  15

```
<210> SEQ ID NO 40
<211> LENGTH: 12
<212> TYPE: PRT
<213> ORGANISM: Artificial sequence
<220> FEATURE:
<223> OTHER INFORMATION: hinge

<400> SEQUENCE: 40

Glu Leu Lys Thr Pro Leu Gly Asp Thr Thr His Thr
1               5                   10

<210> SEQ ID NO 41
<211> LENGTH: 10
<212> TYPE: PRT
<213> ORGANISM: Artificial sequence
<220> FEATURE:
<223> OTHER INFORMATION: hinge

<400> SEQUENCE: 41

Lys Ser Cys Asp Lys Thr His Thr Cys Pro
1               5                   10

<210> SEQ ID NO 42
<211> LENGTH: 7
<212> TYPE: PRT
<213> ORGANISM: Artificial sequence
<220> FEATURE:
<223> OTHER INFORMATION: hinge

<400> SEQUENCE: 42

Lys Cys Cys Val Asp Cys Pro
1               5

<210> SEQ ID NO 43
<211> LENGTH: 7
<212> TYPE: PRT
<213> ORGANISM: Artificial sequence
<220> FEATURE:
<223> OTHER INFORMATION: hinge

<400> SEQUENCE: 43

Lys Tyr Gly Pro Pro Cys Pro
1               5

<210> SEQ ID NO 44
<211> LENGTH: 15
<212> TYPE: PRT
<213> ORGANISM: Artificial sequence
<220> FEATURE:
<223> OTHER INFORMATION: hinge

<400> SEQUENCE: 44

Glu Pro Lys Ser Cys Asp Lys Thr His Thr Cys Pro Pro Cys Pro
1               5                   10                  15

<210> SEQ ID NO 45
<211> LENGTH: 12
<212> TYPE: PRT
<213> ORGANISM: Artificial sequence
<220> FEATURE:
<223> OTHER INFORMATION: hinge

<400> SEQUENCE: 45

Glu Arg Lys Cys Cys Val Glu Cys Pro Pro Cys Pro
1               5                   10
```

```
<210> SEQ ID NO 46
<211> LENGTH: 17
<212> TYPE: PRT
<213> ORGANISM: Artificial sequence
<220> FEATURE:
<223> OTHER INFORMATION: hinge

<400> SEQUENCE: 46

Glu Leu Lys Thr Pro Leu Gly Asp Thr Thr His Thr Cys Pro Arg Cys
1               5                   10                  15

Pro

<210> SEQ ID NO 47
<211> LENGTH: 12
<212> TYPE: PRT
<213> ORGANISM: Artificial sequence
<220> FEATURE:
<223> OTHER INFORMATION: hinge

<400> SEQUENCE: 47

Ser Pro Asn Met Val Pro His Ala His His Ala Gln
1               5                   10

<210> SEQ ID NO 48
<211> LENGTH: 15
<212> TYPE: PRT
<213> ORGANISM: Artificial sequence
<220> FEATURE:
<223> OTHER INFORMATION: hinge

<400> SEQUENCE: 48

Glu Pro Lys Ser Cys Asp Lys Thr Tyr Thr Cys Pro Pro Cys Pro
1               5                   10                  15
```

METHODS TO PROTECT TRANSPLANTED TISSUE FROM REJECTION

CROSS-REFERENCE TO RELATED APPLICATION

The present application is entitled to priority under 35 U.S.C. § 119(e) to U.S. Provisional Patent Application No. 62/477,815, filed Mar. 28, 2017, which is hereby incorporated by reference in its entirety herein.

BACKGROUND OF THE INVENTION

Transplant rejection occurs when the recipient's immune system attacks the transplanted tissue or organ. Rejection is generally mediated by alloreactive T cells present in the recipient which recognize donor alloantigens or xenoantigens. Host T cells can recognize allograft human leukocyte antigen (HLA) or an associated bound peptide. The alloreactive T cells are stimulated by donor antigen presenting cells (APCs) which express both allogeneic MHC and costimulatory activity. Alloreactive CD4+ T cells produce cytokines that exacerbate the cytolytic CD8 response to the alloantigen. Undesirable alloreactive T cell responses in patients (allograft rejection, graft-versus-host disease) are typically handled with immunosuppressive drugs such as prednisone, azathioprine, and cyclosporine A. Unfortunately, these drugs generally need to be maintained for the life of the patient and they have a multitude of dangerous side effects including generalized immunosuppression.

Peripheral blood contains a small population of T cell lymphocytes that express the T regulatory phenotype ("Treg"), i.e., are positive for both CD4 and CD25 antigens. There are several subsets of Treg cells. One subset of regulatory cells develops in the thymus. Thymic derived Treg cells function by a cytokine-independent mechanism, which involves cell to cell contact. They are essential for the induction and maintenance of self-tolerance and for the prevention of autoimmunity. These regulatory cells prevent the activation and proliferation of autoreactive T cells that have escaped thymic deletion or recognize extrathymic antigens, thus they are critical for homeostasis and immune regulation, as well as for protecting the host against the development of autoimmunity. Thus, immune regulatory $CD4^+CD25^+$ T cells are often referred to as "professional suppressor cells."

A need exists for novel compositions and methods that suppress in vivo alloresponses and protect transplanted tissue from rejection. The present invention satisfies this need.

SUMMARY

As described herein, the present invention relates to compositions and methods for utilizing an HLA-A2 specific CAR to protect transplanted tissue from rejection.

In one aspect, the invention includes a modified immune cell or precursor cell thereof, comprising a chimeric antigen receptor (CAR) having affinity for HLA-A2. In some embodiments, the CAR comprises an HLA-A2 binding domain, and a CD8 hinge domain.

Another aspect of the invention includes a modified immune cell or precursor cell thereof, comprising a chimeric antigen receptor (CAR) having affinity for HLA-A2. In some embodiments, the CAR comprises an HLA-A2 binding domain, a CD8 hinge domain, a CD8 signal peptide, a CD28 transmembrane domain, a CD28 costimulatory domain, and a CD3ζ intracellular domain.

The present invention is based on the discovery that genetically modified immune cells comprising an HLA-A2 specific chimeric antigen receptor (CAR) of the invention demonstrate specificity for HLA-A2, HLA-A28 and/or HLA-A68. The present invention is also based on the discovery that genetically modified regulatory T cells comprising a subject HLA-A2 specific CAR demonstrate potent immunosuppressive effects.

Accordingly, in certain aspects, the present invention provides a modified immune cell or precursor cell thereof, comprising a chimeric antigen receptor (CAR) having affinity for HLA-A2.

In one aspect, a modified immune cell or precursor cell thereof, comprising a chimeric antigen receptor (CAR) having affinity for HLA-A2, wherein the CAR comprises an HLA-A2 binding domain, is provided.

In certain exemplary embodiments, the CAR further comprises a signal peptide.

In certain exemplary embodiments, the signal peptide is a CD8 signal peptide.

In certain exemplary embodiments, the CAR further comprises a hinge domain.

In certain exemplary embodiments, the hinge domain is a CD8 hinge domain.

In certain exemplary embodiments, the HLA-A2 binding domain is selected from the group consisting of an antibody, a Fab, or an scFv.

In certain exemplary embodiments, the HLA-A2 binding domain comprises a heavy chain variable region comprising the amino acid sequence set forth in SEQ ID NO: 3.

In certain exemplary embodiments, the HLA-A2 binding domain comprises a light chain variable region comprising the amino acid sequence set forth in SEQ ID NO: 8.

In certain exemplary embodiments, the HLA-A2 binding domain comprises a spacer sequence.

In certain exemplary embodiments, the HLA-A2 binding domain comprises the amino acid sequence set forth in SEQ ID NO: 1.

In certain exemplary embodiments, the CAR comprises a transmembrane domain, and an intracellular domain.

In certain exemplary embodiments, the transmembrane domain comprises a CD28 transmembrane domain.

In certain exemplary embodiments, the transmembrane domain comprises the amino acid sequence set forth in SEQ ID NO: 17.

In certain exemplary embodiments, the intracellular domain comprises a CD28 intracellular domain, and a CD3ζ intracellular domain.

In certain exemplary embodiments, the CD28 intracellular domain comprises the amino acid sequence set forth in SEQ ID NO: 19.

In certain exemplary embodiments, the CD3ζ intracellular domain comprises the amino acid sequence set forth in SEQ ID NO: 21.

In certain exemplary embodiments, the CD8 hinge comprises the amino acid sequence set forth in SEQ ID NO: 15.

In certain exemplary embodiments, the CD8 signal peptide comprises the amino acid sequence set forth in SEQ ID NO: 13.

In certain exemplary embodiments, the CAR comprises the amino acid sequence set forth in SEQ ID NO: 23.

In certain exemplary embodiments, wherein the HLA-A2 binding domain cross-reacts with HLA-A28.

In certain exemplary embodiments, the HLA-A2 binding domain cross-reacts with HLA-A68.

In certain exemplary embodiments, the modified cell is a modified regulatory T cell.

In certain exemplary embodiments, the modified cell is an autologous cell.

In certain exemplary embodiments, the modified cell is derived from a human.

In another aspect, a modified immune cell or precursor cell thereof, comprising a chimeric antigen receptor (CAR) having affinity for HLA-A2, wherein the CAR comprises a CD8 signal peptide, HLA-A2 binding domain, a CD8 hinge domain, a CD28 transmembrane domain, a CD28 costimulatory domain, and a CD3ζ intracellular domain, is provided.

In certain exemplary embodiments, the CAR comprises the amino acid sequence set forth in SEQ ID NO: 23.

In certain exemplary embodiments, wherein the HLA-A2 binding domain cross-reacts with HLA-A28.

In certain exemplary embodiments, the HLA-A2 binding domain cross-reacts with HLA-A68.

In certain exemplary embodiments, the modified cell is a modified regulatory T cell.

In certain exemplary embodiments, the modified cell is an autologous cell.

In certain exemplary embodiments, the modified cell is derived from a human.

In another aspect, an isolated nucleic acid, comprising a nucleic acid sequence encoding a chimeric antigen receptor (CAR) having affinity for HLA-A2, wherein the CAR comprises an HLA-A2 binding domain, is provided.

In certain exemplary embodiments, the CAR further comprises a signal peptide.

In certain exemplary embodiments, the signal peptide is a CD8 signal peptide. In certain exemplary embodiments, the CAR further comprises a hinge domain.

In certain exemplary embodiments, the hinge domain is a CD8 hinge domain.

In certain exemplary embodiments, an isolated nucleic acid, comprising a nucleic acid sequence encoding a chimeric antigen receptor (CAR) having affinity for HLA-A2, wherein the CAR comprises a CD8 signal peptide, an HLA-A2 binding domain, and a CD8 hinge domain, is provided.

In certain exemplary embodiments, the CAR comprises a CD28 transmembrane domain.

In certain exemplary embodiments, the CAR comprises a CD28 costimulatory domain.

In certain exemplary embodiments, the CAR comprises a CD3ζ intracellular domain.

In certain exemplary embodiments, the isolated nucleic acid comprises the nucleic acid sequence set forth in SEQ ID NO: 24. In another aspect, an expression construct comprising the isolated nucleic acid of the aspects described herein, is provided.

In certain exemplary embodiments, the expression construct comprises an EF-1α promoter.

In certain exemplary embodiments, the expression construct comprises a rev response element (RRE).

In certain exemplary embodiments, the expression construct comprises a woodchuck hepatitis virus posttranscriptional regulatory element (WPRE).

In certain exemplary embodiments, the expression construct comprises a cPPT sequence.

In certain exemplary embodiments, the expression construct comprises an EF-1α promoter, a rev response element (RRE), a woodchuck hepatitis virus posttranscriptional regulatory element (WPRE), and a cPPT sequence.

In certain exemplary embodiments, the expression construct is a viral vector selected from the group consisting of a retroviral vector, a lentiviral vector, an adenoviral vector, and an adeno-associated viral vector.

In certain exemplary embodiments, the expression construct is a lentiviral vector. In certain exemplary embodiments, the lentiviral vector is a self-inactivating lentiviral vector.

In another aspect, a method for generating the modified immune cell or precursor cell thereof of the aspects described herein, comprising introducing into the immune cell the nucleic acid of the aspects described herein, or the expression construct of the aspects described herein, is provided.

In another aspect, a method for achieving an immunosuppressive effect in a subject in need thereof, comprising administering to the subject an effective amount of the modified immune cell or precursor cell thereof of the aspects described herein, is provided.

In certain exemplary embodiments, the subject is suffering from an alloresponse and/or an autoimmune response.

In certain exemplary embodiments, the alloresponse or autoimmune response follows tissue transplantation, and wherein the method suppresses, blocks, or inhibits graft-vs-host-disease in the subject.

In certain exemplary embodiments, the modified cell is a modified regulatory T cell.

In certain exemplary embodiments, the modified cell is an autologous cell.

In certain exemplary embodiments, the modified cell is derived from a human.

In another aspect, a method for achieving a preventative therapeutic effect in a subject in need thereof, comprising administering to the subject, prior to onset of an alloresponse or autoimmune response, an effective amount of the modified immune cell or precursor cell thereof of the aspects described herein, is provided.

In certain exemplary embodiments, the alloresponse or autoimmune response follows tissue transplantation, and wherein the method suppresses, blocks, or inhibits graft-vs-host-disease in the subject.

In certain exemplary embodiments, the modified cell is a modified regulatory T cell.

In certain exemplary embodiments, the modified cell is an autologous cell.

In certain exemplary embodiments, the modified cell is derived from a human.

In another aspect, a method for achieving an immunosuppressive effect, in a subject in need thereof having an alloresponse or autoimmune response, comprising administering to the subject a modified regulatory T cell comprising a chimeric antigen receptor (CAR) having affinity for HLA-A2, wherein the CAR comprises a CD8 signal peptide, an HLA-A2 binding domain, a CD8 hinge domain, a CD28 transmembrane domain, a CD28 costimulatory domain, and a CD3ζ intracellular domain, is provided.

In certain exemplary embodiments, the alloresponse or autoimmune response follows tissue transplantation, and wherein the method suppresses, blocks, or inhibits graft-vs-host-disease in the subject.

In certain exemplary embodiments, the modified cell is a modified regulatory T cell.

In certain exemplary embodiments, the modified cell is an autologous cell.

In certain exemplary embodiments, the modified cell is derived from a human.

In another aspect, a method of treating diabetes in a subject in need thereof, comprising administering to the subject an effective amount of the modified immune cell or precursor cell thereof of the aspects described herein, is provided.

In certain exemplary embodiments, the diabetes is type 1 diabetes.

In certain exemplary embodiments, the modified cell is a modified regulatory T cell.

In certain exemplary embodiments, the modified cell is an autologous cell.

In certain exemplary embodiments, the modified cell is derived from a human.

In another aspect, a method of treating diabetes in a subject in need thereof, comprising administering to the subject a modified regulatory T cell comprising a chimeric antigen receptor (CAR) having affinity for HLA-A2, wherein the CAR comprises a CD8 signal peptide, an HLA-A2 binding domain, a CD8 hinge domain, a CD28 transmembrane domain, a CD28 costimulatory domain, and a CD3ζ intracellular domain, is provided.

In certain exemplary embodiments, the diabetes is type 1 diabetes.

In certain exemplary embodiments, the modified cell is a modified regulatory T cell.

In certain exemplary embodiments, the modified cell is an autologous cell.

In certain exemplary embodiments, the modified cell is derived from a human.

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

DETAILED DESCRIPTION

Definitions

Figure 1:
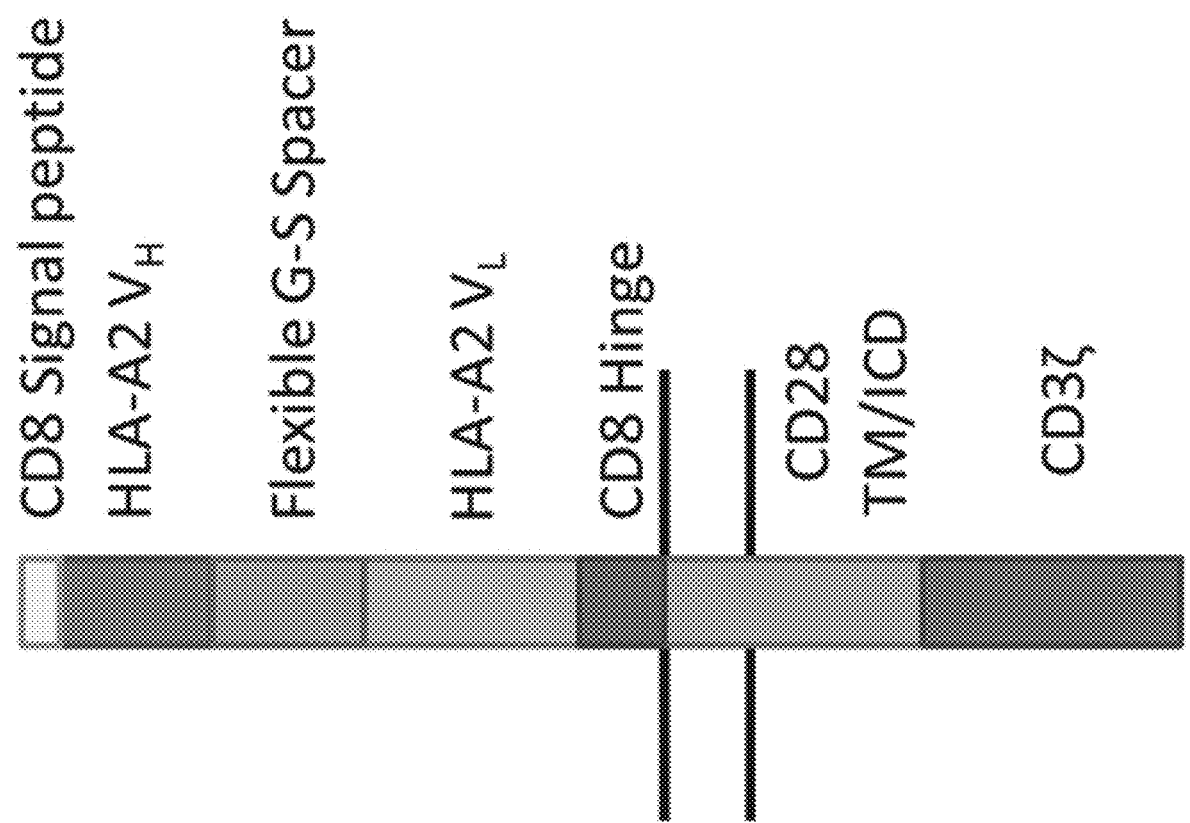
FIG. 1 is a schematic of an HLA-A2 specific CAR which, when expressed on human T regulatory cells, mediates antigen specific suppression.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

"Allogeneic" refers to a graft derived from a different animal of the same species.

"Alloantigen" refers to an antigen present only in some individuals of a species and capable of inducing the production of an alloantibody by individuals which lack it.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CAR has specificity to a selected target, for example a human leukocyte antigen (HLA). CARs may also comprise an intracellular activation domain, a transmembrane domain and an extracellular domain comprising an antigen binding region. In some aspects, CARs comprise an extracellular domain comprising an anti-HLA binding domain fused to CD8 hinge domain, a CD28 transmembrane and intracellular domain, and a CD3-zeta domain.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation.

Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Donor antigen" refers to an antigen expressed by the donor tissue to be transplanted into the recipient.

"Recipient antigen" refers to a target for the immune response to the donor antigen.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size.

Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"HLA-A2" refers to a human leukocyte antigen within the HLA-A serotype group. HLA-A is one of the three major types of MHC class I cell surface receptors. MHC class I molecules are one of two primary classes of major histocompatibility complex (MHC) molecules that are found on the cell surface of cells. The function of MHC class I molecules is to display peptide fragments of non-self proteins from within the cell to immune cells (e.g., cytotoxic T cells), resulting in the trigger of an immediate response from the immune system against the particular non-self-antigen that is displayed.

"HLA-A28" refers to a human leukocyte antigen within the HLA-A serotype group.

"HLA-A68" refers to a human leukocyte antigen within the HLA-A serotype group. The alpha "A" chain is encoded by the HLA-A*68 allele group and the β-chain is encoded by the β-2 microglobulin (B2M) locus.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

The term "immunostimulatory" is used herein to refer to increasing overall immune response.

The term "immunosuppressive" is used herein to refer to reducing overall immune response.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

"Xenogeneic" refers to any material derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention includes compositions and methods for utilizing an HLA-A2 specific CAR to protect transplanted tissue from rejection. The HLA-A2 specific CAR comprises an antigen binding domain that binds to HLA-A2, HLA-A28, and/or HLA-A68. When expressed on human T regulatory cells (Tregs), the HLA-A2 specific CAR mediates antigen specific suppression. The HLA-A2 specific CAR is able to redirect T regulatory cells to HLA-A2, HLA-A28, and/or HLA-A68 expressing tissue and mediate tolerance.

The present invention includes an HLA-A2 specific CAR and its use in suppressing alloresponses. Alloresponses are provoked during, e.g., organ transplantation, by donor-MHC class I molecules which are ubiquitously expressed in allografts. The present invention is based on the finding that regulatory T cells comprising an HLA-A2 specific CAR are capable of suppressing alloresponses in an antigen-specific manner.

Chimeric Antigen Receptor (CAR)

The present invention provides compositions and methods for modified immune cells or precursor cells thereof, e.g., modified regulatory T cells, comprising a chimeric antigen receptor (CAR) having affinity for HLA-A2. A subject CAR of the invention comprises an antigen binding domain (e.g., HLA-A2 binding domain), a transmembrane domain, and an intracellular domain. A subject CAR of the invention may optionally comprise a hinge domain, and/or a signal peptide. In some embodiments, the signal peptide is a CD8 signal peptide. Accordingly, a subject CAR of the invention comprises an antigen binding domain (e.g., HLA-A2 binding domain), a hinge domain, a transmembrane domain, and an intracellular domain. In some embodiments, a subject CAR of the invention comprises a signal peptide, an antigen binding domain (e.g., HLA-A2 binding domain), a hinge domain, a transmembrane domain, and an intracellular domain. In some embodiments, each of the domains of a subject CAR is separated by a linker.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention.

In one aspect, the invention includes an isolated HLA-A2 specific chimeric antigen receptor (CAR) comprising a CD8 signal peptide, an HLA-A2 VH domain, a spacer sequence, an HLA-A2 VL domain, a CD8 hinge region, a CD28 transmembrane domain, a CD28 costimulatory domain, and a CD3-zeta intracellular domain. In another aspect, the invention includes an isolated nucleic acid encoding an HLA-A2 specific CAR, wherein the CAR comprises a CD8 signal peptide, an HLA-A2 VH domain, a spacer sequence, an HLA-A2 VL domain, a CD8 hinge region, a CD28 transmembrane domain, a CD28 costimulatory domain, and a CD3-zeta intracellular domain. Another aspect of the invention includes an isolated polypeptide comprising a CD8 signal peptide, an HLA-A2 VH domain, a spacer sequence, an HLA-A2 VL domain, a CD8 hinge region, a CD28 transmembrane domain, and a CD3-zeta intracellular domain.

Another aspect of the invention includes a genetically modified T cell comprising an isolated nucleic acid encoding an HLA-A2 specific CAR, wherein the CAR comprises a CD8 signal peptide, an HLA-A2 VH domain, a spacer sequence, an HLA-A2 VL domain, a CD8 hinge region, a CD28 transmembrane domain, a CD28 costimulatory domain, and a CD3-zeta intracellular domain. In some embodiments, a genetically modified immune cell (e.g., T cell) of the present invention comprises an HLA-A2 CAR, wherein the CAR comprises a CD8 signal peptide, an HLA-A2 VH domain, a spacer sequence, an HLA-A2 VL domain, a CD8 hinge, a CD28 transmembrane domain, a CD28 costimulatory domain, and a CD3-zeta intracellular domain. In some embodiments, a genetically modified immune cell (e.g., T cell) or precursor cell thereof of the present invention comprises a chimeric antigen receptor (CAR) having affinity for HLA-A2. The CAR comprises an HLA-A2 binding domain, a CD8 hinge domain, a CD8 signal peptide, a CD28 transmembrane domain, a CD28 costimulatory domain, and a CD3ζ intracellular domain.

In certain embodiments of the invention, the CAR is encoded by the nucleic acid sequence of SEQ ID NO: 24. In other embodiments, the CAR comprises the amino acid sequence of SEQ ID NO: 23.

In certain embodiments, the genetically modified T cell is a T regulatory (Treg) cell.

Sequences of individual domains are found in Table 1.

TABLE 1

| SEQ ID NO: | Description | Sequence |
|---|---|---|
| 1 | HLA-A2 scFv amino acid sequence | QVQLVQSGGGVVQPGGSLRVSCAASGVTLSDYGMHWVRQAPG KGLEWMAFIRNDGSDKYYADSVKGRFTISRDNSKKTVSLQMSSL RAEDTAVYYCAKNGESGPLDYWYFDLWGRGTLVTVSGGGGSG GGGSGGGGSDVVMTQSPSSLSASVGDRVTITCQASQDISNYLNW YQQKPGKAPKLLIYDASNLETGVPSRFSGSGSGTDFTFTISSLQPE DFATYYCQQYSSFPLTFGGGTKVDIKR |
| 2 | HLA-A2 scFv nucleic acid sequence | caggtgcagctggtgcagtctggggggaggcgtggtccagcctggggggtccctgagagtctcctgtg cagcgtctgggggtcaccctcagtgattatggcatgcattgggtccgccaggctccaggcaaggggctg gagtggatggcttttatacggaatgatggaagtgataaatattatgcagactccgtgaagggccgattca ccatctccagagacaactccaagaaaacagtgtctctgcaaatgagcagtctcagagctgaagacacg gctgtgtattactgtgcgaaaaatggcgaatctgggcctaggactactggtacttcgatctctggggccg tggcaccctggtcaccgtgtcgggtggcggtggctcgggtggtggtggtggcggcggatc tgatgttgtgatgactcagtctccatcctccctgtctgcatctgtaggagacagagtcccatcacttgcc aggcgagtcaggacattagcaactatttaaattggtatcagcagaaaccagggaaagcccctaagctc ctgatctacgatgcatccaataggaaacaggggtcccatcaaggttcagtggaagtggatctgggaca gatttttactacaccatcagcagcctgcagcctgaggattttgcaacttattactgccaacaatatagtagtt tccgctcacttttcggcggagggaccaaagtggatatcaaacgt |
| 3 | HLA-A2 scFv heavy chain (HC) variable region amino acid sequence | QVQLVQSGGGVVQPGGSLRVSCAASGVTLSDYGMHWVRQAPG KGLEWMAFIRNDGSDKYYADSVKGRFTISRDNSKKTVSLQMSSL RAEDTAVYYCAKNGESGPLDYWYFDLWGRGT |
| 4 | HLA-A2 scFv HC variable region nucleic acid sequence | caggtgcagctggtgcagtctggggggaggcgtggtccagcctggggggtccctgagagtctcctgtg cagc gtctgggggtcaccctcagtgattatggcatgcattgggtccgccaggctccaggcaaggggctg gagtggatggcttttatacggaatgatggaagtgataaatattatgcagactccgtgaagggccgattca ccatctccagagacaactccaagaaaacagtgtctctgcaaatgagcagtctcagagctgaagacacg gctgtgtattactgtgcgaaaaatggcgaatctgggcctggactactggtacttcgatctctggggccg tggcacc |
| 5 | HLA-A2 scFv HC CDR1 amino acid sequence | DYGMH |
| 6 | HLA-A2 scFv HC CDR2 amino acid sequence | FIRNDGSDKYYADSVKG |
| 7 | HLA-A2 scFv HC CDR3 amino acid sequence | NGESGPLDYWYFDL |
| 8 | HLA-A2 scFv light chain (LC) variable region amino acid sequence | DVVMTQSPSSLSASVGDRVTITCQASQDISNYLNWYQQKPGKAP KLLIYDASNLETGVPSRFSGSGSGTDFTFTISSLQPEDFATYYCQQ YSSFPLTFGGGTKVDIKR |
| 9 | HLA-A2 scFv LC variable region nucleic acid sequence | gatgttgtgatgactcagtctccatcctccctgtctgcatctgtaggagacagagtcaccatcacttgcca ggcgagtcaggacattagcaactatttaaattggtatcagcagaaaccagggaaagcccctaagctcct gatctacgatgcatccaatttggaaacaggggtcccatcaaggttcagtggaagtggatctgggacag atttttactttcaccatcagcagcctgcagcctgaggattttgcaacttattactgccaacaatatagtagtttt ccgctcacttttcggcggagggaccaaagtggatatcaaacgt |
| 10 | HLA-A2 scFv LC CDR1 amino acid sequence | QASQDISNYLN |

TABLE 1-continued

| SEQ ID NO: | Description | Sequence |
|---|---|---|
| 11 | HLA-A2 scFv LC CDR2 amino acid sequence | DASNLET |
| 12 | HLA-A2 scFv LC CDR3 amino acid sequence | QQYSSFPLT |
| 13 | CD8 signal peptide amino acid sequence | MALPVTALLLPLALLLHAARP |
| 14 | CD8 signal peptide nucleic acid sequence | atggccttaccagtgaccgccttgctcctgccgctggccttgctgctccacgccgccaggccg |
| 15 | CD8 hinge amino acid sequence | TTTPAPRPPTPAPTIASQPLSLRPEACRPAAGGAVHTRGLDFACD |
| 16 | CD8 hinge nucleic acid sequence | accacgacgccagcgccgcgaccaccaacaccggcgcccaccatcgcgtcgcagcccctgtccct gcgcccagaggcgtgccggccagcggcggggggcgcagtgcacacgagggggctggacttcgcc tgtgat |
| 17 | CD28 transmembrane domain amino acid sequence | FWVLVVVGGVLACYSLLVTVAFIIFWV |
| 18 | CD28 transmembrane domain nucleic acid sequence | ttagggtgctggtggtggttggtggagtcctggcttgctatagcttgctagtaacagtggcctttattatta ctgggtg |
| 19 | CD28 intracellular domain amino acid sequence | RSKRSRLLHSDYMNMTPRRPGPTRKHYQPYAPPRDFAAYRS |
| 20 | CD28 intracellular domain nucleic acid sequence | aggagtaagaggagcaggctcctgcacagtgactacatgaacatgactccccgccgccccgggccc acccgcaagcattaccagccctatgccccaccacgcgacttcgcagcctatcgctcc |
| 21 | CD3 zeta domain amino acid sequence | RVKFSRSADAPAYQQGQNQLYNELNLGRREEYDVLDKRRGRDP EMGGKPRRKNPQEGLYNELQKDKMAEAYSEIGMKGERRRGKG HDGLYQGLSTATKDTYDALHMQALPPR |
| 22 | CD3 zeta domain nucleic acid sequence | agagtgaagttcagcaggagcgcagacgcccccgcgtaccagcagggccagaaccagctctataac gagctcaatctaggacgaagagaggagtacgatgttaggacaagagacgtggccgggaccctgaga tgggggggaaagccgagaaggaagaaccctcaggaaggcctgtacaatgaactgcagaaagataag atggcggaggcctacagtgagattgggatgaaaggcgagcgccggaggggcaaggggcacgatg gcctttaccagggtctcagtacagccaccaaggacacctacgacgcccttcacatgcaggccctgccc cctcgc |
| 23 | HLA-A2 CAR amino acid sequence | MALPVTALLLPLALLLHAARPGSQVQLVQSGGGVVQPGGSLRVS CAASGVTLSDYGMHWVRQAPGKGLEWMAFIRNDGSDKYYADS VKGRFTISRDNSKKTVSLQMSSLRAEDTAVYYCAKNGESGPLDY WYFDLWGRGTLVTVSGGGGSGGGGSGGGGSDVVMTQSPSSLSA SVGDRVTITCQASQDISNYLNWYQQKPGKAPKLLIYDASNLETG VPSRFSGSGSGTDFTFTISSLQPEDFATYYCQQYSSFPLTFGGGTK VDIKRSGTTTPAPRPPTPAPTIASQPLSLRPEACRPAAGGAVHTRG LDFACDFWVLVVVGGVLACYSLLVTVAFIIFWVRSKRSRLLHSD YMNMTPRRPGPTRKHYQPYAPPRDFAAYRSIDRVKFSRSADAPA YQQGQNQLYNELNLGRREEYDVLDKRRGRDPEMGGKPRRKNP QEGLYNELQKDKMAEAYSEIGMKGERRRGKGHDGLYQGLSTAT KDTYDALHMQALPPR |
| 24 | HLA-A2 CAR nucleic acid sequence | ATGGCCTTACCAGTGACCGCCTTGCTCCTGCCGCTGGCCTTGC TGCTCCACGCCGCCAGGCCGGGATCCCAGGTGCAGCTGGTGC AGTCTGGGGGAGGCGTGGTCCAGCCTGGGGGGTCCCTGAGAG TCTCCTGTGCAGCGTCTGGGGTCACCCTCAGTGATTATGGCAT GCATTGGGTCCGCCAGGCTCCAGGCAAGGGGCTGGAGTGGAT GGCTTTTATACGGAATGATGGAAGTGATAAATATTATGCAGA CTCCGTGAAGGGCCGATTCACCATCTCCAGAGACAACTCCAA GAAAACAGTGTCTCTGCAAATGAGCAGTCTCAGAGCTGAAGA CACGGCTGTGTATTACTGTGCGAAAAATGGCGAATCTGGGCC |

TABLE 1-continued

| SEQ ID NO: | Description | Sequence |
|---|---|---|
| | | TTTGGACTACTGGTACTTCGATCTCTGGGGCCGTGGCACCCTG<br>GTCACCGTGTCGGGTGGCGGTGGCTCGGGCGGTGGTGGGTCG<br>GGTGGCGGCGGATCTGATGTTGTGATGACTCAGTCTCCATCCT<br>CCCTGTCTGCATCTGTAGGAGACAGAGTCACCATCACTTGCCA<br>GGCGAGTCAGGACATTAGCAACTATTTAAATTGGTATCAGCA<br>GAAACCAGGGAAAGCCCCTAAGCTCCTGATCTACGATGCATC<br>CAATTTGGAAACAGGGGTCCCATCAAGGTTCAGTGGAAGTGG<br>ATCTGGGACAGATTTTACTTTCACCATCAGCAGCCTGCAGCCT<br>GAGGATTTTGCAACTTATTACTGCCAACAATATAGTAGTTTTC<br>CGCTCACTTTCGGCGGAGGGACCAAAGTGGATATCAAACGTT<br>CCGGAACCACGACGCCAGCGCCGCGACCACCAACACCGGCGC<br>CCACCATCGCGTCGCAGCCCCTGTCCCTGCGCCCAGAGGCGTG<br>CCGGCCAGCGGCGGGGGCGCAGTGCACACGAGGGGGCTGG<br>ACTTCGCCTGTGATTTTTGGGTGCTGGTGGTGGTTGGTGGAGT<br>CCTGGCTTGCTATAGCTTGCTAGTAACAGTGGCCTTTATTATTT<br>TCTGGGTGAGGAGTAAGAGGAGCAGGCTCCTGCACAGTGACT<br>ACATGAACATGACTCCCCGCCGCCCCGGGCCCACCCGCAAGC<br>ATTACCAGCCCTATGCCCCACCACGCGACTTCGCAGCCTATCG<br>CTCCATCGATAGAGTGAAGTTCAGCAGGAGCGCAGACGCCC<br>CGCGTACCAGCAGGGCCAGAACCAGCTCTATAACGAGCTCAA<br>TCTAGGACGAAGAGAGGAGTACGATGTTTTGGACAAGAGACG<br>TGGCCGGGACCCTGAGATGGGGGGAAAGCCGAGAAGGAAGA<br>ACCCTCAGGAAGGCCTGTACAATGAACTGCAGAAAGATAAGA<br>TGGCCGGAGGCCTACAGTGAGATTGGGATGAAAGGCGAGCGCC<br>GGAGGGGCAAGGGGCACGATGGCCTTTACCAGGGTCTCAGTA<br>CAGCCACCAAGGACACCTACGACGCCCTTCACATGCAGGCCC<br>TGCCCCCTCGC |

Accordingly, a subject CAR may be a CAR having affinity for HLA-A2, comprising an HLA-A2 binding domain comprising an amino acid sequence set forth in SEQ ID NO: 1 A subject HLA-A2 CAR may further comprise a hinge domain comprising an amino acid sequence set forth in SEQ ID NO: 15. A subject HLA-A2 CAR may further comprise a transmembrane domain comprising an amino acid sequence set forth in SEQ ID NO: 17. A subject HLA-A2 CAR may further comprise an intracellular domain comprising an amino acid sequence set forth in SEQ ID NO: 17. A subject HLA-A2 CAR may comprise an amino acid sequence set forth in SEQ ID NO: 23.

In certain embodiments, a subject HLA-A2 CAR of the present invention comprises affinity for HLA-A2, HLA-A28 and/or HLA-A68 independent of peptide presentation by these MHC class I molecules. For example, in certain embodiments, the specificity of a subject HLA-A2 CAR of the present invention is not influenced by the presentation of any peptide by the HLA-A2 molecule.

Antigen Binding Domain

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular status of the target cell.

In one embodiment, the CAR of the invention comprises an antigen binding domain that binds to HLA-A2, HLA-A28 and/or HLA-A68. In another embodiment, the antigen binding domain of the invention comprises an antibody or fragment thereof, that binds to an HLA-A2, HLA-A28, and/or HLA-A68 molecule. Preferably, the antigen binding domain is an scFv antibody that binds to an HLA-A2, HLA-A28, and/or HLA-A68 molecule. The choice of antigen binding domain depends upon the type and number of antigens that are present on the surface of a target cell. For example, the antigen binding domain may be chosen to recognize an antigen that acts as a cell surface marker on a target cell associated with a particular status of the target cell.

As described herein, a CAR of the present disclosure having affinity for a specific target antigen on a target cell may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In an exemplary embodiment, a CAR of the present disclosure having affinity for HLA-A2 on a target cell may comprise a HLA-A2 binding domain. In some embodiments, the HLA-A2 binding domain is a murine HLA-A2 binding domain, e.g., the HLA-A2 binding domain is of murine origin. In some embodiments, the HLA-A2 binding domain is a humanized HLA-A2 binding domain. In some embodiments, the HLA-A2 binding domain is a human HLA-A2 binding domain, e.g., the HLA-A2 binding domain is of human origin.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multispecific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof. In another embodiment, the antigen binding domain of the CAR is selected from the group consisting of an anti-HLA-A2 antibody or a fragment thereof. In some embodiments, the antigen binding domain is selected from the group consisting of an antibody, an antigen binding fragment (Fab), and a single-chain variable fragment (scFv). In some embodiments, a HLA-A2 binding domain of the present invention is selected from the group consisting of a HLA-A2-specific antibody, a HLA-A2-specific Fab, and a HLA-A2-specific scFv. In one embodiment, a HLA-A2 binding domain is a HLA-A2-specific antibody. In one embodiment, a HLA-A2 binding domain is a HLA-A2-specific Fab. In one embodiment, a HLA-A2 binding domain is a HLA-A2-specific scFv.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., HLA-A2 binding domain) comprises an scFv having the configuration from N-terminus to C-terminus, VH-linker-VL. In some embodiments, the antigen binding domain (e.g., HLA-A2 binding domain) comprises an scFv having the configuration from N-terminus to C-terminus, VL-linker VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO: 25), $(GGGS)_n$ (SEQ ID NO: 26), and $(GGGGS)_n$ (SEQ ID NO: 27), where n represents an integer of at least 1. Exemplary linker sequences can comprise amino acid sequences including, without limitation, GGSG (SEQ ID NO: 28), GGSGG (SEQ ID NO: 29), GSGSG (SEQ ID NO: 30), GSGGG (SEQ ID NO: 31), GGGSG (SEQ ID NO: 32), GSSSG (SEQ ID NO: 33), GGGGS (SEQ ID NO: 34), GGGGSGGGGSGGGGS (SEQ ID NO: 35) and the like. Those of skill in the art would be able to select the appropriate linker sequence for use in the present invention. In one embodiment, an antigen binding domain (e.g., HLA-A2 binding domain) of the present invention comprises a heavy chain variable region (VH) and a light chain variable region (VL), wherein the VH and VL is separated by the linker sequence having the amino acid sequence GGGGSGGGGSGGGGS (SEQ ID NO: 35), which may be encoded by the nucleic acid sequence ggtggcggtggctcggggcggtggtgggtcgggtggcggcggatct (SEQ ID NO: 36).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some instances, the antigen binding domain may be derived from the same species in which the CAR will ultimately be used. For example, for use in humans, the antigen binding domain of the CAR may comprise a human antibody as described elsewhere herein, or a fragment thereof.

In an exemplary embodiment, an HLA-A2 CAR of the present invention comprises an HLA-A2 binding domain, e.g., an HLA-A2-specific scFv. In one embodiment, the HLA-A2 binding domain comprises the amino acid sequence set forth in SEQ ID NO: 1.

In one embodiment, the HLA-A2 binding domain comprises a light chain variable region comprising an amino acid sequence set forth in SEQ ID NO: 8. The light chain variable region of the HLA-A2 binding domain comprises three light chain complementarity-determining regions (CDRs). As used herein, a "complementarity-determining region" or "CDR" refers to a region of the variable chain of an antigen binding molecule that binds to a specific antigen. Accordingly, an HLA-A2 binding domain may comprise a light chain variable region that comprises a CDR1 comprising an amino acid sequence set forth in SEQ ID NO: 10; a CDR2 comprising an amino acid sequence set forth in SEQ ID NO: 11; and a CDR3 comprising an amino acid sequence set forth in SEQ ID NO: 12.

In one embodiment, the HLA-A2 binding domain comprises a heavy chain variable region comprising an amino acid sequence set forth in SEQ ID NO: 3. An HLA-A2 binding domain may comprise a heavy chain variable region that comprises a CDR1 comprising an amino acid sequence set forth in SEQ ID NO: 5; a CDR2 comprising an amino acid sequence set forth in SEQ ID NO: 6; and a CDR3 comprising an amino acid sequence set forth in SEQ ID NO: 7.

Tolerable variations of the HLA-A2 binding domain will be known to those of skill in the art, while maintaining specific binding to HLA-A2. For example, in some embodiments the HLA-A2 binding domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 3, 5-8, and 10-12. For example, in some embodiments the HLA-A2 binding domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleic acid sequences set forth in SEQ ID NOs: 2, 4, and 9.

The antigen binding domain may be operably linked to another domain of the CAR, such as the transmembrane domain or the intracellular domain, both described elsewhere herein. In one embodiment, a nucleic acid encoding the antigen binding domain is operably linked to a nucleic acid encoding a transmembrane domain and a nucleic acid encoding an intracellular domain.

The antigen binding domains described herein, such as the antibody or fragment thereof that binds to HLA-A2, HLA-A28, and/or HLA-A68, can be combined with any of the transmembrane domains described herein, any of the intracellular domains or cytoplasmic domains described herein, or any of the other domains described herein that may be included in the CAR.

Transmembrane Domain

With respect to the transmembrane domain, the CAR of the present invention (e.g., HLA-A2 CAR) can be designed to comprise a transmembrane domain that connects the antigen binding domain of the CAR to the intracellular domain. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane regions of particular use in this invention include, without limitation, transmembrane domains derived from (i.e. comprise at least the transmembrane region(s) of) the alpha, beta or zeta chain of the T-cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In some embodiments, the transmembrane domain further comprises a hinge region. A subject CAR of the present invention may also include an hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

For example, hinge regions include glycine polymers $(G)_n$, glycine-serine polymers (including, for example, $(GS)_n$, $(GSGGS)_n$ (SEQ ID NO: 25) and $(GGGS)_n$ (SEQ ID NO: 26), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, Rev. Computational. Chem. (1992) 2: 73-142). Exemplary hinge regions can comprise amino acid sequences including, but not limited to, GGSG (SEQ ID NO: 28), GGSGG (SEQ ID NO: 29), GSGSG (SEQ ID NO: 30), GSGGG (SEQ ID NO: 31), GGGSG (SEQ ID NO: 32), GSSSG (SEQ ID NO: 33), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acids Res.* (1986) 14(4): 1779-1789. As non-limiting examples, an immunoglobulin hinge region can include one of the following amino acid sequences: DKTHT (SEQ ID NO: 37); CPPC (SEQ ID NO: 38); CPEPKSCDTPPPCPR (SEQ ID NO: 39) (see, e.g., Glaser et al., *J Biol. Chem.* (2005) 280:41494-41503); ELKTPLGDTTHT (SEQ ID NO: 40); KSCDKTHTCP (SEQ ID NO: 41); KCCVDCP (SEQ ID NO: 42); KYGPPCP (SEQ ID NO: 43); EPKSCDKTHTCPPCP (SEQ ID NO: 44) (human IgG1 hinge); ERKCCVECPPCP (SEQ ID NO: 45) (human IgG2 hinge); ELKTPLGDTTH-TCPRCP (SEQ ID NO: 46) (human IgG3 hinge); SPNMVPHAHHAQ (SEQ ID NO: 47) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO: 48); see, e.g., Yan et al., *J. Biol. Chem.* (2012) 287: 5891-5897. In one embodiment, the hinge region can comprise an amino acid sequence derived from human CD8, or a variant thereof.

In one embodiment, the transmembrane domain comprises a CD28 transmembrane domain. In another embodiment, the transmembrane domain comprises a CD8 hinge domain and a CD28 transmembrane domain. In some embodiments, a subject CAR comprises a CD8 hinge region having the amino acid sequence set forth in SEQ ID NO: 15, which may be encoded by the nucleic acid sequence set forth in SEQ ID NO: 16. In some embodiments, a subject CAR comprises a CD28 transmembrane domain having the amino acid sequence set forth in SEQ ID NO: 17, which may be encoded by the nucleic acid sequence set forth in SEQ ID NO: 18. In some embodiments, the transmembrane domain comprises a CD8 hinge region and a CD28 transmembrane domain.

Tolerable variations of the transmembrane and/or hinge domain will be known to those of skill in the art, while maintaining its intended function. For example, in some embodiments the hinge domain and/or transmembrane domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 15 and/or 17. For example, in some embodiments the hinge domain and/or transmembrane domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleic acid sequences set forth in SEQ ID NOs: 16 and/or 18.

The transmembrane domain may be combined with any hinge domain and/or may comprise one or more transmembrane domains described herein.

The transmembrane domains described herein, such as a transmembrane region of alpha, beta or zeta chain of the T-cell receptor, CD28, CD3 epsilon, CD45, CD4, CD5, CD7, CD8, CD9, CD 16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9, can be combined with any of the antigen binding domains described herein, any of the intracellular domains or cytoplasmic domains described herein, or any of the other domains described herein that may be included in the CAR.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the intracellular domain in the polypeptide chain. A spacer domain may comprise up to 300 amino acids, e.g., 10 to 100 amino acids, or 25 to 50 amino acids. In some embodiments, the spacer domain may be a short oligo- or polypeptide linker, e.g., between 2 and 10 amino acids in length. For example, glycine-serine doublet provides a particularly suitable linker between the transmembrane domain and the intracellular signaling domain of the subject CAR.

Intracellular Domain

A subject CAR of the present invention also includes an intracellular signaling domain. The terms "intracellular signaling domain" and "intracellular domain" are used interchangeably herein. The intracellular signaling domain of the CAR is responsible for activation of at least one of the effector functions of the cell in which the CAR is expressed (e.g., immune cell). The intracellular signaling domain transduces the effector function signal and directs the cell (e.g., immune cell) to perform its specialized function, e.g., harming and/or destroying a target cell.

The intracellular domain or otherwise the cytoplasmic domain of the CAR includes a similar or the same intracellular domain as the chimeric intracellular signaling molecule described elsewhere herein, and is responsible for activation of the cell in which the CAR is expressed. In one embodiment, the intracellular domain comprises CD3 zeta. In another embodiment, the intracellular domain comprises CD28 and CD3 zeta.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular signaling domain include, without limitation, the ζ chain of the T cell receptor complex or any of its homologs, e.g., η chain, FcεRIγ and β chains, MB 1 (Iga) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcεRI, cytoplasmic tails of Fc receptors, an immunoreceptor tyrosine-based activation motif (ITAM) bearing cytoplasmic receptors, and combinations thereof.

In one embodiment, the intracellular domain of the CAR includes any portion of one or more co-stimulatory molecules, such as at least one signaling domain from CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP 12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD127, CD 160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD 103, ITGAL, CD 11 a, LFA-1, ITGAM, CD lib, ITGAX, CD 11c, ITGB1, CD29, ITGB2, CD 18, LFA-1, ITGB7, TNFR2, TRANCE/RANKL, DNAM1 (CD226), SLAMF4 (CD244, 2B4), CD84, CD 96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular signaling domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, FcgammaRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCER1G (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

In one embodiment, the intracellular domain of a subject CAR comprises a CD28 intracellular domain comprising the amino acid sequence set forth in SEQ ID NO: 19, which may be encoded by the nucleic acid sequence set forth in SEQ ID NO: 20. In one embodiment, the intracellular domain of a subject CAR comprises a CD3 zeta domain comprising the amino acid sequence set forth in SEQ ID NO: 21, which may be encoded by the nucleic acid sequence set forth in SEQ ID NO: 22. In one exemplary embodiment, the intracellular domain of a subject CAR comprises a CD28 domain and a CD3 zeta domain.

Tolerable variations of the intracellular domain will be known to those of skill in the art, while maintaining specific activity. For example, in some embodiments the intracellular domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 19 and/or 21. For example, in some embodiments the intracellular domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleic acid sequences set forth in SEQ ID NOs: 20 and/or 22.

In another embodiment, a spacer domain may be incorporated between the antigen binding domain and the transmembrane domain of the CAR, or between the intracellular domain and the transmembrane domain of the CAR. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

CAR Sequences

A subject CAR of the present invention may be a CAR having affinity for HLA-A2. In one embodiment, the HLA-A2 CAR of the present invention comprises the amino acid sequence set forth in SEQ ID NO: 23, which may be encoded by the nucleic acid sequence set forth in SEQ ID NO: 24.

Tolerable variations of the CAR will be known to those of skill in the art, while maintaining specific activity. For example, in some embodiments the CAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NO: 23. For example, in some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 24.

Accordingly, a subject CAR of the present invention comprises an HLA-A2 binding domain and a transmembrane domain. In one embodiment, the CAR comprises an HLA-A2 binding domain and a transmembrane domain, wherein the transmembrane domain comprises a CD8 hinge region. In one embodiment, the CAR comprises an HLA-A2 binding domain and a transmembrane domain, wherein the transmembrane domain comprises a CD28 transmembrane domain. In one embodiment, the CAR comprises an HLA-A2 binding domain and a transmembrane domain, wherein the transmembrane domain comprises a CD8 hinge region and a CD28 transmembrane domain.

Accordingly, a subject CAR of the present invention comprises an HLA-A2 binding domain, a transmembrane domain, and an intracellular domain. In one embodiment, the CAR comprises an HLA-A2 binding domain, a transmembrane domain, and an intracellular domain, wherein the intracellular domain comprises a CD28 domain. In one embodiment, the CAR comprises an HLA-A2 binding domain, a transmembrane domain, and an intracellular domain, wherein the intracellular domain comprises a CD3 zeta domain. In one embodiment, the CAR comprises an HLA-A2 binding domain, a transmembrane domain, and an intracellular domain, wherein the intracellular domain comprises a CD28 domain and a CD3 zeta domain.

Accordingly, a subject CAR of the present invention comprises an HLA-A2 binding domain, a CD8 hinge region, a CD28 transmembrane domain, a CD28 intracellular domain, and a CD3 zeta intracellular domain.

Accordingly, the present invention provides a modified immune cell or precursor cell thereof, e.g., a modified regulatory T cell, comprising a chimeric antigen receptor (CAR) having affinity for HLA-A2 as described herein.

Human Antibodies

It may be preferable that the antigen binding domains of the CAR comprise human antibodies or fragments thereof. Fully human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as MI 3 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13 (5): 353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8): 1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences.

Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

Nucleic Acids and Expression Vectors

The present invention provides a nucleic acid encoding a CAR having affinity for HLA-A2. As described herein, a subject CAR comprises an antigen binding domain (e.g., HLA-A2 binding domain), a transmembrane domain, and an intracellular domain. Accordingly, the present invention provides a nucleic acid encoding an antigen binding domain (e.g., HLA-A2 binding domain), a transmembrane domain, and an intracellular domain of a subject CAR.

In an exemplary embodiment, a nucleic acid encoding an HLA-A2 CAR of the present invention is encoded by a nucleic acid sequence set forth in SEQ ID NO: 24.

In some embodiments, a nucleic acid of the present disclosure may be operably linked to a transcriptional control element, e.g., a promoter, and enhancer, etc. Suitable promoter and enhancer elements are known to those of skill in the art.

For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999) 67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as Escherichia coli include, but are not limited to Trc, Tac, T5, T7, and PLambda. Non-limiting examples of operators for use in bacterial host cells include a lactose promoter operator (Lad repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the EF-1 alpha promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released upon CAR signaling. See, e.g., Chmielewski and Abken, Expert Opin. Biol. Ther. (2015) 15(8): 1145-1154; and Abken, Immunotherapy (2015) 7(5): 535-544.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in any way as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRITS (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549; Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648; Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617); SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR into an immune cell or precursor thereof (e.g., a T cell). Accordingly, an expression vector (e.g., a lentiviral vector) of the present invention may comprise a nucleic acid encoding a CAR. In some embodiments, the expression vector (e.g., lentiviral vector) will comprise additional elements that will aid in the functional expression of the CAR encoded therein. In some embodiments, an expression vector comprising a nucleic acid encoding a CAR further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a CAR encoding nucleic acid sequence). Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a posttranscriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR of the present disclosure. Methods for introducing RNA into a host cell are known in the art. See, e.g., Zhao et al. *Cancer Res.* (2010) 15: 9053. Introducing RNA comprising a nucleotide sequence encoding a CAR of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

Methods of Generating Modified Immune Cells

The present invention provides methods for producing/generating a modified immune cell or precursor cell thereof (e.g., a regulatory T cell). The cells are generally engineered by introducing a nucleic acid encoding a subject CAR (e.g., HLA-A2 CAR).

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

In some embodiments, a nucleic acid encoding a subject CAR of the invention is introduced into a cell by an expression vector. Expression vectors comprising a nucleic acid encoding a subject CAR (e.g., HLA-A2 CAR) are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the subject CAR in the host cell. In some embodiments, the adenovirus genome is a 36 kb, linear, double stranded DNA, where a foreign DNA sequence (e.g., a nucleic acid encoding a subject CAR) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus, which takes advantage of the adenovirus coupled systems. This AAV expression vector has a high frequency of integration into the host genome. It can infect non-dividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., a nucleic acid encoding a subject CAR) into the viral genome at certain locations to produce a virus that is replication defective. Though the retrovirus vectors are able to infect a broad variety of cell types, integration and stable expression of the subject CAR, requires the division of host cells.

Lentivirus vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression, e.g., of a nucleic acid encoding a subject CAR (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell is an immune cell or precursor thereof, e.g., a T cell, an NK cell, or an NKT cell.

The present invention also provides genetically engineered cells which include and stably express a subject CAR of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In one embodiment, the genetically engineered cells are autologous cells.

Modified cells (e.g., comprising a subject CAR) may be produced by stably transfecting host cells with an expression vector including a nucleic acid of the present disclosure. Additional methods to generate a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a subject CAR of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the host cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

PCR can be used to generate a template for in vitro transcription of mRNA which is then introduced into cells.

Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of host cell activity in basic research and therapy, in the fields of cancer, stem cells, acute and chronic infections, and autoimmune diseases, including the assessment of the ability of the genetically modified host cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of host cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of Immune Cells

Prior to expansion, a source of immune cells is obtained from a subject for ex vivo manipulation. Sources of target cells for ex vivo manipulation may also include, e.g., autologous or heterologous donor blood, cord blood, or bone marrow. For example, the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell, a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune cells are obtained from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker$^-$) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNA-BEADS® M-450 CD3/CD28 T Cell Expander).

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L-subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and/or a CD8+T population is enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+T helper cells are sorted into naive, central memory, and effector cells by identifying cell populations that have cell surface antigens. CD4+ lymphocytes can be obtained by standard methods. In some embodiments, naive CD4+T lymphocytes are CD45RO-, CD45RA+, CD62L+, CD4+ T cells. In some embodiments, central memory CD4+ cells are CD62L+ and CD45RO+. In some embodiments, effector CD4+ cells are CD62L- and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In another embodiment, T cells are isolated from peripheral blood by lysing the red blood cells and depleting the monocytes, for example, by centrifugation through a PERCOLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

Expansion of Immune Cells

Whether prior to or after modification of cells to express a subject CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the immune cells of the invention may be expanded by contact with a surface having attached thereto an agent that stimulates a CD3/TCR complex associated signal and a ligand that stimulates a co-stimulatory molecule on the surface of the immune cells. In particular, immune cell populations may be stimulated by contact with an anti-CD3 antibody, or an antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the immune cells, a ligand that binds the accessory molecule is used. For example, immune cells can be contacted with an anti-CD3 antibody and an anti-CD28 antibody, under conditions appropriate for stimulating proliferation of the immune cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding the immune cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the immune cells expand in the range of about 20 fold to about 50 fold.

Following culturing, the immune cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The immune cell medium may be replaced during the culture of the immune cells at any time. Preferably, the immune cell medium is replaced about every 2 to 3 days. The immune cells are then harvested from the culture apparatus whereupon the immune cells can be used immediately or cryopreserved to be stored for use at a later time. In one embodiment, the invention includes cryopreserving the expanded immune cells. The cryopreserved immune cells are thawed prior to introducing nucleic acids into the immune cell.

In another embodiment, the method comprises isolating immune cells and expanding the immune cells. In another embodiment, the invention further comprises cryopreserving the immune cells prior to expansion. In yet another embodiment, the cryopreserved immune cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of immune cells comprises the addition to the cellular growth factors, such as those described in U.S. Pat. No. 5,199,942, or other factors, such as flt3-L, IL-1, IL-3 and c-kit ligand. In one embodiment, expanding the immune cells comprises culturing the immune cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for immune cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the immune cells may include an agent that can co-stimulate the immune cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the immune cells expand in the range of about 20 fold to about 50 fold, or more by culturing the electroporated population. In one embodiment, human T regulatory cells are expanded via anti-CD3 antibody coated KT64.86 artificial antigen presenting cells (aAPCs). Methods for expanding and activating immune cells can be found in U.S. Pat. Nos. 7,754,482, 8,722,400, and 9,555,105, contents of which are incorporated herein in their entirety.

In one embodiment, the method of expanding the immune cells can further comprise isolating the expanded immune cells for further applications. In another embodiment, the method of expanding can further comprise a subsequent electroporation of the expanded immune cells followed by culturing. The subsequent electroporation may include introducing a nucleic acid encoding an agent, such as a transducing the expanded immune cells, transfecting the expanded immune cells, or electroporating the expanded immune cells with a nucleic acid, into the expanded population of immune cells, wherein the agent further stimulates the immune cell. The agent may stimulate the immune cells, such as by stimulating further expansion, effector function, or another immune cell function.

Methods of Treatment

The modified immune cells (e.g., regulatory T cells) described herein may be included in a composition for immunotherapy, in particular suppression immunotherapy. The composition may include a pharmaceutical composition and further include a pharmaceutically acceptable carrier. A therapeutically effective amount of the pharmaceutical composition comprising the modified immune cells may be administered.

In one aspect, the invention includes a method for adoptive cell transfer therapy comprising administering to a subject in need thereof a modified immune cell (e.g., regulatory T cell) of the present invention. In another aspect, the invention includes a method of treating a disease or a condition in a subject comprising administering to a subject in need thereof a population of modified immune cells.

In one embodiment, the method of treating a disease or condition in a subject in need thereof comprises administering to the subject a therapeutically effective amount of a modified Treg comprising a subject CAR (e.g., HLA-A2 CAR). In one embodiment, the method of treating a disease or condition in a subject in need thereof comprises administering to the subject a therapeutically effect amount of a modified Treg comprising a subject CAR (e.g., HLA-A2 CAR), wherein the subject CAR comprises an antigen binding domain that can bind to HLA-A2, HLA-A28, and/or HLA-A68. In one embodiment, the HLA-A2 specific CAR comprises a CD8 signal peptide, an HLA-A2 $V_H$ domain, a spacer sequence, an HLA-A2 $V_L$ domain, a CD8 hinge region, a CD28 transmembrane domain, a CD28 costimulatory domain, and a CD3ζ intracellular domain.

The HLA-A2 CAR of the invention is able to redirect immune cells (e.g., regulatory T cells) to targets expressing the HLA-A2 alloantigen. As such, the subject CAR of the invention is an alloantigen-specific CAR. Tregs expressing an HLA-A2 CAR of the invention upon activation by HLA-A2 binding, induces proliferation of the modified Tregs and enhances the suppressor function of the modified Tregs.

When a modified immune cell comprising a subject CAR of the invention is administered, the transplanted tissue is protected from rejection. In one embodiment, a modified immune cell comprising a subject CAR of the invention (e.g., a Treg comprising an HLA-A2 CAR) can mediate HLA-A2-specific immunosuppression. In one embodiment, a modified immune cell comprising a subject CAR of the invention (e.g., a Treg comprising an HLA-A2 CAR) can suppress T cell proliferation in response to allogeneic antigens (e.g., HLA-A2 antigen). In some embodiments, upon cell, tissue, and/or organ transplantation, HLA-A2 may be ubiquitously expressed on the transplanted cells, tissues, and/or organs. In such cases, substantial immune cell infiltration into the transplanted cells, tissues, and/or organs may occur, resulting in destruction of the transplanted cells, tissues, and/or organs. Accordingly, in some embodiments, a modified immune cell comprising a subject CAR of the invention (e.g., a Treg comprising an HLA-A2 CAR), is capable of reducing infiltration of immune cells, and thus protecting the transplanted cells, tissues, and/or organs from destruction. In some cases, the transplanted cells, tissues, and/or organs may mediate toxicity. Accordingly, in some embodiments, a modified immune cell comprising a subject CAR of the invention (e.g., a Treg comprising an HLA-A2 CAR), is able to reduce transplanted cells, tissues, and/or organ-mediated toxicity.

Accordingly, the present invention provides a method for achieving a preventative therapeutic effect in a subject in need thereof, and/or a method for achieving an immunosuppressive effect in a subject in need thereof e.g. one who is experiencing and/or suffering from an alloresponse or autoimmune response. In some embodiments, a method for achieving a preventative therapeutic effect in a subject in need thereof, and/or a method for achieving an immunosuppressive effect in a subject in need thereof with an alloresponse or autoimmune response, comprises administering to the subject a modified immune cell comprising a subject CAR of the invention. In one embodiment, the present invention provides a method for achieving an immunosuppressive effect in a subject in need thereof with an alloresponse or autoimmune response, comprising administering to the subject a modified regulatory T cell comprising a chimeric antigen receptor (CAR) having affinity for HLA-A2, wherein the CAR comprises an HLA-A2 binding domain, a CD8 hinge domain, a CD28 transmembrane domain, a CD28 costimulatory domain, and a CD3ζ intracellular domain. In one embodiment, the present invention provides a method for achieving a preventative therapeutic effect in a subject in need thereof, comprising administering to the subject a modified regulatory T cell comprising a chimeric antigen receptor (CAR) having affinity for HLA-A2, wherein the CAR comprises an HLA-A2 binding domain, a CD8 hinge domain, a CD28 transmembrane domain, a CD28 costimulatory domain, and a CD3ζ intracellular domain.

Type 1 diabetes is a T cell-mediated autoimmune disease resulting in islet beta-cell destruction, hypoinsulinemia, and severely altered glucose homeostasis. Failure of regulatory T cells (Tregs) may play a role in the development of type 1 diabetes. During immune homeostasis, Tregs counterbalance the actions of autoreactive effector T cells, thereby participating in peripheral tolerance. Thus, an imbalance between effector T cells and Tregs may contribute to the breakdown of peripheral tolerance, leading to the development of type 1 diabetes. In some embodiments, a modified immune cell comprising a subject CAR of the invention (e.g., a Treg comprising an HLA-A2 CAR), is capable of suppressing T cell-mediated autoimmune diseases, such as type 1 diabetes.

Accordingly, the present invention provides a method of treating diabetes in a subject in need thereof, comprising administering to the subject a modified immune cell comprising a subject CAR of the invention. In some embodiments, a method of treating diabetes in a subject in need thereof is provided, comprising administering to the subject a modified regulatory T cell comprising a chimeric antigen receptor (CAR) having affinity for HLA-A2, wherein the CAR comprises an HLA-A2 binding domain, a CD8 hinge domain, a CD28 transmembrane domain, a CD28 costimulatory domain, and a CD3ζ intracellular domain. In some embodiments, the diabetes is type I diabetes.

In certain embodiments, the CAR is encoded by the nucleic acid sequence of SEQ ID NO: 24. In certain embodiments, the CAR comprises the amino acid sequence of SEQ ID NO: 23.

In certain embodiments, the modified immune cell is a modified regulatory T cell (Treg). In some embodiments, the modified immune cell is an autologous cell. In some embodiments, the modified immune cell (e.g., modified regulatory T cell) is derived from a human.

The CAR can redirect the T regulatory cell to HLA-A2, HLA-A28, and/or HLA-A68 expressing tissue, thus enhancing protection of the transplanted tissue from rejection. The T cell comprising a nucleic acid encoding an HLA-A2 specific can be administered to the subject prior to, at the time of, or immediately after tissue transplantation.

The methods of the present invention should be construed to include protection from rejection of any type of transplanted organ, tissue, or cells, including but not limited to lungs, hearts, heart valves, skin, liver, hand, kidneys, pancreas, intestines, stomach, thymus, bones, tendons, cornea, testes, nerves, veins, blood, bone marrow, stem cells, islets of Langerhans cells, and hematopoietic cells. The methods of the invention also include protection against graft versus host disease (GVHD).

In certain embodiments, the subject can be administered, in addition to the CAR, a secondary treatment, such as an immunosuppressive drug. Examples of immunosuppressive drugs include but are not limited to prednisone, azathioprine, tacrolimus, and cyclosporine A.

PHARMACEUTICAL COMPOSITIONS

Pharmaceutical compositions of the present invention may comprise the modified immune cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

Also provided are populations of immune cells of the invention, compositions containing such cells and/or enriched for such cells, such as in which cells expressing the recombinant receptor make up at least 50%, 60%, 70%, 80%, 90%, 91%, 92%, 93%, 94%, 95%, 96%, 97%, 98%, 99%, or more of the total cells in the composition or cells of a certain type such as regulatory T cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980).

Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount.

Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

It can generally be stated that a pharmaceutical composition comprising the modified immune cells described herein may be administered at a dosage of $10^4$ to $10^9$ cells/kg body weight, in some instances $10^5$ to $10^6$ cells/kg body weight, including all integer values within those ranges. Immune cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified immune cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i. v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in these experiments are now described. 3PF12 antibody was derived from: Watkins et al., The isolation and characterization of human monoclonal HLA-A2 antibodies from an immune V gene phage display library. (2000). doi:10.1034/j.1399-0039.2000.550305.

```
HLA-A2 specific CAR nucleotide sequence:
                                    (SEQ ID NO: 24)
ATGGCCTTACCAGTGACCGCCTTGCTCCTGCCGCTGGCCTTGCTGCTCCA

CGCCGCCAGGCCGGGATCCCAGGTGCAGCTGGTGCAGTCTGGGGGAGGCG

TGGTCCAGCCTGGGGGGTCCCTGAGAGTCTCCTGTGCAGCGTCTGGGGTC

ACCCTCAGTGATTATGGCATGCATTGGGTCCGCCAGGCTCCAGGCAAGGG

GCTGGAGTGGATGGCTTTTATACGGAATGATGGAAGTGATAAATATTATG

CAGACTCCGTGAAGGGCCGATTCACCATCTCCAGAGACAACTCCAAGAAA

ACAGTGTCTCTGCAAATGAGCAGTCTCAGAGCTGAAGACACGGCTGTGTA

TTACTGTGCGAAAAATGGCGAATCTGGGCCTTTGGACTACTGGTACTTCG

ATCTCTGGGGCCGTGGCACCCTGGTCACCGTGTCGGGTGGCGGTGGCTCG

GGCGGTGGTGGGTCGGGTGGCGGCGGATCTGATGTTGTGATGACTCAGTC

TCCATCCTCCCTGTCTGCATCTGTAGGAGACAGAGTCACCATCACTTGCC

AGGCGAGTCAGGACATTAGCAACTATTTAAATTGGTATCAGCAGAAACCA

GGGAAAGCCCCTAAGCTCCTGATCTACGATGCATCCAATTTGGAAACAGG
```

```
                              -continued
GGTCCCATCAAGGTTCAGTGGAAGTGGATCTGGGACAGATTTTACTTTCA

CCATCAGCAGCCTGCAGCCTGAGGATTTTGCAACTTATTACTGCCAACAA

TATAGTAGTTTTCCGCTCACTTTCGGCGGAGGGACCAAAGTGGATATCAA

ACGTTCCGGAACCACGACGCCAGCGCCGCGACCACCAACACCGGCGCCCA

CCATCGCGTCGCAGCCCCTGTCCCTGCGCCCAGAGGCGTGCCGGCCAGCG

GCGGGGGGCGCAGTGCACACGAGGGGGCTGGACTTCGCCTGTGATTTTTG

GGTGCTGGTGGTGGTTGGTGGAGTCCTGGCTTGCTATAGCTTGCTAGTAA

CAGTGGCCTTTATTATTTTCTGGGTGAGGAGTAAGAGGAGCAGGCTCCTG

CACAGTGACTACATGAACATGACTCCCCGCCGCCCCGGGCCCACCCGCAA

GCATTACCAGCCCTATGCCCCACCACGCGACTTCGCAGCCTATCGCTCCA

TCGATAGAGTGAAGTTCAGCAGGAGCGCAGACGCCCCCGCGTACCAGCAG

GGCCAGAACCAGCTCTATAACGAGCTCAATCTAGGACGAAGAGAGGAGTA

CGATGTTTTGGACAAGAGACGTGGCCGGGACCCTGAGATGGGGGGAAAGC

CGAGAAGGAAGAACCCTCAGGAAGGCCTGTACAATGAACTGCAGAAAGAT

AAGATGGCGGAGGCCTACAGTGAGATTGGGATGAAAGGCGAGCGCCGGAG

GGGCAAGGGGCACGATGGCCTTTACCAGGGTCTCAGTACAGCCACCAAGG

ACACCTACGACGCCCTTCACATGCAGGCCCTGCCCCCTCGCTAA

HLA-A2 specific CAR amino acid sequence:
                                    (SEQ ID NO: 23)
MALPVTALLLPLALLLHAARPGSQVQLVQSGGGVVQPGGSLRVSCAASGV

TLSDYGMHWVRQAPGKGLEWMAFIRNDGSDKYYADSVKGRFTISRDNSKK

TVSLQMSSLRAEDTAVYYCAKNGESGPLDYWYFDLWGRGTLVTVSGGGGS

GGGGSGGGGSDVVMTQSPSSLSASVGDRVTITCQASQDISNYLNVVYQQK

PGKAPKLLIYDASNLETGVPSRFSGSGSGTDFTFTISSLQPEDFATYYCQ

QYSSFPLTFGGGTKVDIKRSGTTTPAPRPPTPAPTIASQPLSLRPEACRP

AAGGAVHTRGLDFACDFWVLVVVGGVLACYSLLVTVAFIIFWVRSKRSRL

LHSDYMNMTPRRPGPTRKHYQPYAPPRDFAAYRSIDRVKFSRSADAPAYQ

QGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR*
```

The results of the experiments are now described.

Herein, an HLA-A2 specific chimeric antigen receptor (CAR) was generated. The HLA-A2 specific CAR comprises an antigen binding domain that can bind HLA-A2, HLA-A28, and/or HLA-A68. When expressed on human regulatory cells (Tregs), the CAR can mediate antigen specific suppression. This novel CAR can redirect Tregs to HLA-A2, HLA-A28, and/or HLA-A68 expressing tissue and mediate tolerance.

In one embodiment, the CAR comprises an extracellular domain comprising a CD8 signal peptide, an HLA-A2 $V_H$ domain, a flexible G-S spacer sequence, an HLA-A2 $V_L$ domain, a CD8 hinge region, a CD28 transmembrane/intracellular domain, and a CD3ζ domain (FIG. 1). In another embodiment, the CAR is encoded by the nucleotide sequence of SEQ ID NO: 24. In yet another embodiment, the CAR comprises the amino acid sequence of SEQ ID NO: 23. The CAR was assembled from the primary amino acid sequence of the 3PF12 scFv detailed in Watkins et al. (2000) doi:10.1034/j.1399-0039.2000.550305. The heavy and light chains were separated by a flexible G-S linker, and put into lentiviral vector pTRPE. The vector contains a CD8 signal peptide to direct the CAR to the cell surface, a CD8 hinge region for CAR flexibility, and the CD28 transmembrane/intracellular domain plus CD3 domain for signaling.

The CAR of the present invention is distinguishable from the CAR of MacDonald et al. (*J Clin Invest.* 2016; 126(4): 1413-142; and *J Immunol May* 1, 2016, 196 (1 Supplement) 140.6), which is derived from the BB7.2 hybridoma, rather than 3PF12, contains a myc tag after the scFv domain, and lacks the CD8 hinge domain. Likewise, in contrast to the CAR of the present invention, the CAR from Boardman et al. (*American Journal of Transplantation.* 2016 Dec. 1]) is derived from the 3PB2 sequence in Watkins et al. ((2000) doi:10.1034/j.1399-0039.2000.550305), rather than the 3PF12, contains a myc tag after the scFv domain, lacks the CD8 hinge domain, and contains eGFP following the signaling domain.

Example 1: HLA-A2 Specific T Cells

Figure 2:
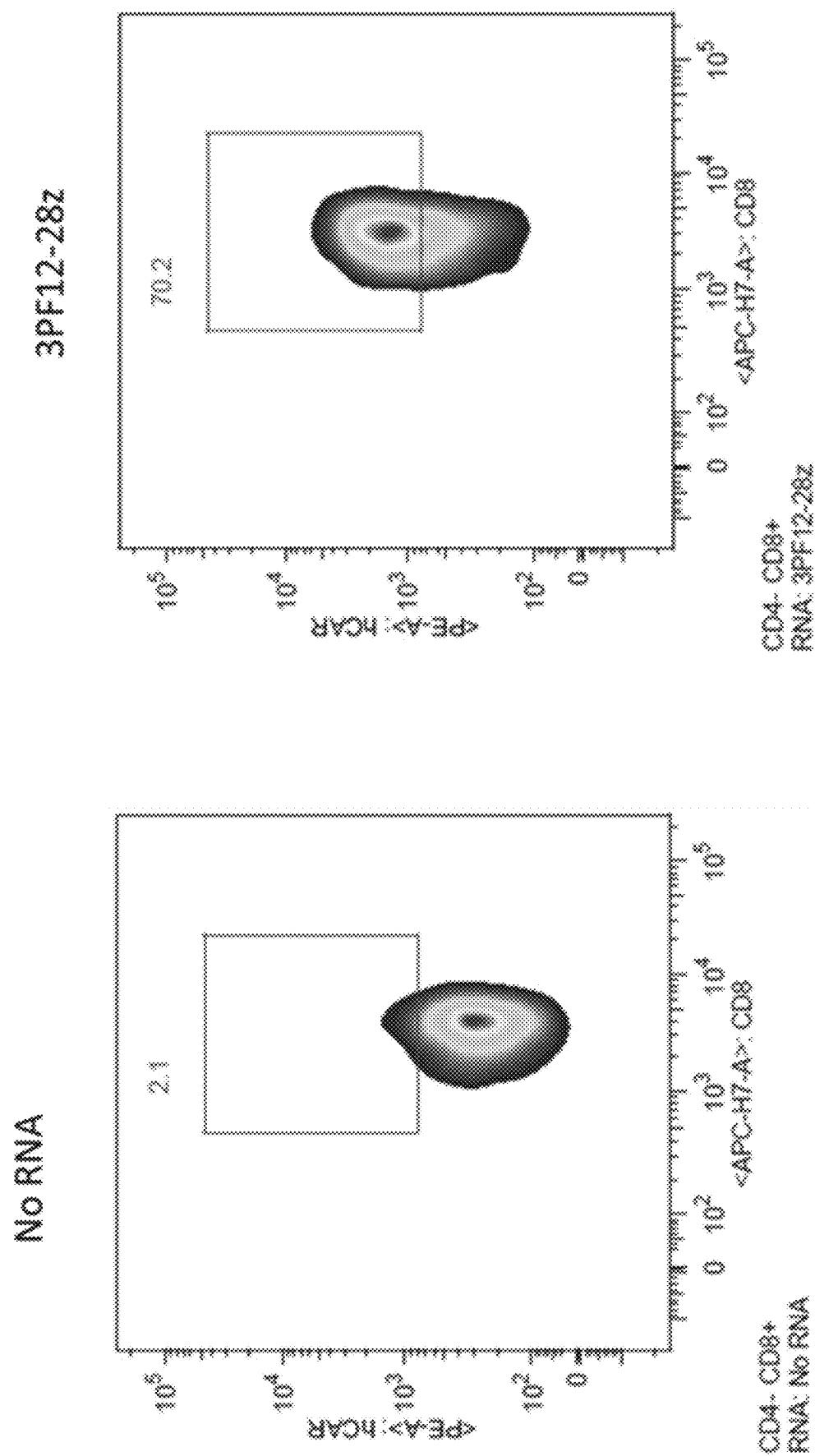
FIG. 2 is a set of plots illustrating primary, human CD8+ T cells that were washed three times in OPTI-MEM reduced serum medium, resuspended at $100 \times 10^6$ cells/mL, mixed with 10 μg of in vitro transcribed HLA-A2 specific CAR encoding RNA, and electroporated. Sixteen hours later, cells were stained with anti-Biotin-SP (long spacer) AffiniPure Goat Anti-Human IgG, F(ab')$_2$ fragment specific, followed by Streptavidin-PE and anti-human CD8. Cells were fixed in 2% paraformaldehyde and analyzed on an LSRII flow cytometer.

Primary, human CD8+ T cells were isolated from normal donor apheresis product by incubating them with RosetteSep reagent for 20 minutes at room temperature, followed layering of the cells on top of Lymphoprep, and centrifuging at 400×g for 30 minutes at room temperature. The cells were then washed three times in OPTI-MEM reduced serum medium (Thermo Fisher Scientific), resuspended at $100 \times 10^6$ cells/mL in OPTI-MEM, mixed with 10 µg of in vitro transcribed 3PF12-28z RNA, and electroporated with a BTX830 (Harvard Apparatus BTX) at 500V for 700 µs in a 0.2 cm electroporation cuvette in vitro RNA transcription was performed with the mMessage mMachine T7 transcription kit (ThermoFisher Scientific) according to manufacturer's instructions, and cleaned up with RNeasy MinElute Clean Up Kit (Qiagen). Cells were incubated in a 37° C./5% $CO_2$ incubator for sixteen hours before being stained with anti-Biotin-SP (long spacer) AffiniPure Goat Anti-Human IgG, $F(ab')_2$ fragment specific antibody on ice for 30 minutes (Jackson Labs), followed by three washes in PBS, and another 30 minute incubation with 1 µL Streptavidin-PE and 1 µL anti-human CD8-APC-H7 (BD Biosciences) diluted in PBS. Cells were fixed in 2% paraformaldehyde and analyzed on an LSRII flow cytometer (BD Biosciences) (FIG. 2). Cells electroporated with 3PF12-28z RNA showed detectable CAR expression on the cell surface.

Figure 3:
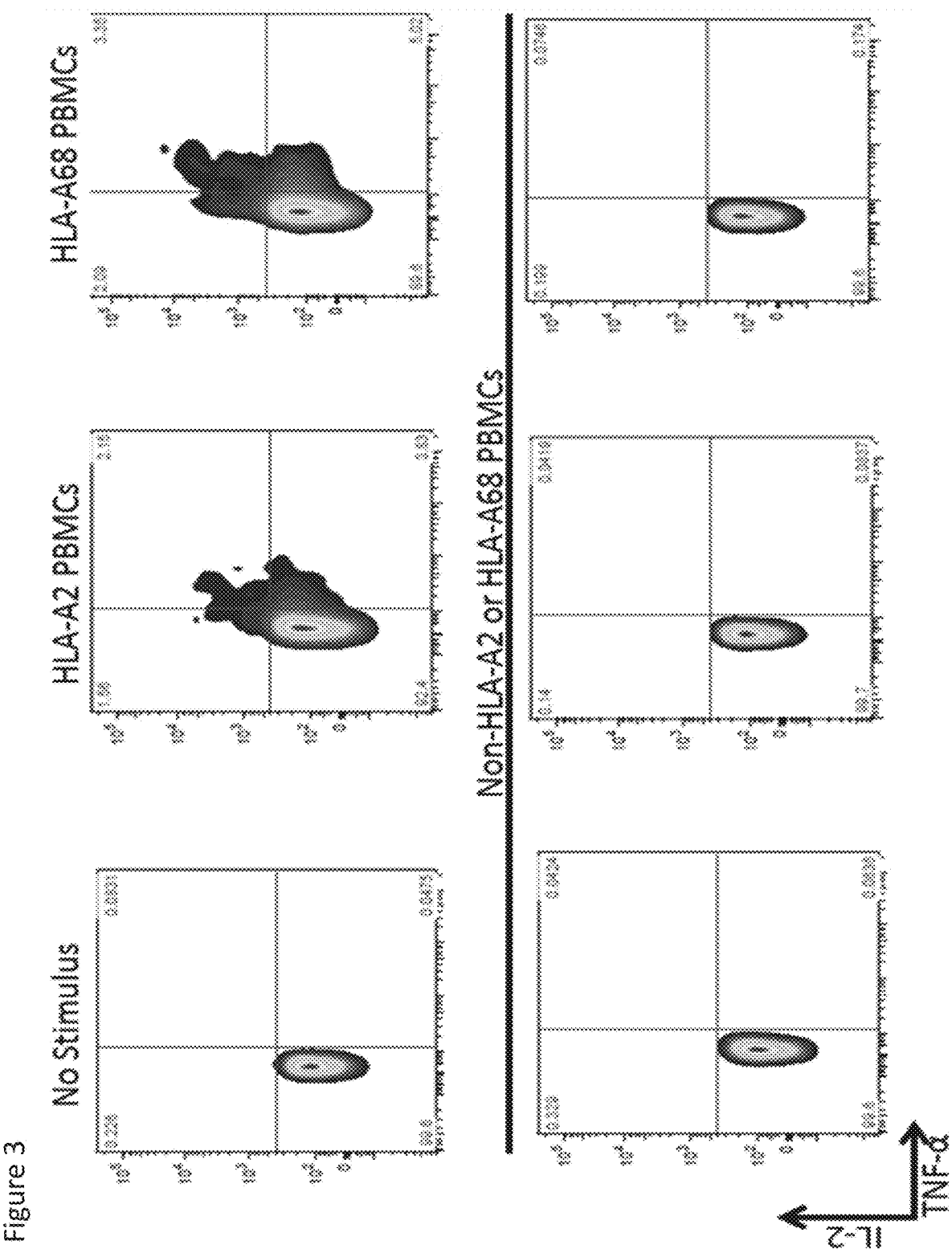
FIG. 3 is a set of plots depicting cells electroporated as in FIG. 2 and mixed in a 3:1 ratio with human donor PBMCs of different HLA haplotypes for 6 hours in the presence of GolgiPlug Protein Transport Inhibitor. Cells were fixed, permeabilized, and stained with α-IL-2 and α-TNF-α antibodies.

Cells that had been electroporated as in FIG. 2 were mixed in a 3:1 ratio with thawed, allogeneic human donor PBMCs of distinct HLA haplotypes for 6 hours in the presence of GolgiPlug Protein Transport Inhibitor (BD Biosciences) in a 37° C./5% $CO_2$ incubator. Cells were then fixed and permeabilized by incubating the cells with 100 pt of Fixation Medium A (ThermoFisher Scientific) for 30 minutes at room temperature, washed and then and stained with 3 µL α-IL-2-APC and 2 µL α-TNF-α-PE-Cy7 antibodies (BD Biosciences) diluted in 100 µL of Fixation Medium B (ThermoFisher Scientific). Cells were then washed with PBS and analyzed on an LSR II flow cytometer (FIG. 3). The CAR+CD8+ T cells were activated by the HLA-A2 and HLA-A68 molecules on the surface of target PBMCs, causing production of IL-2 and TNF-α. In contrast, CAR+CD8+ T cells were not activated by PBMCs from three separate HLA-A2- and HLA-A68-donors, demonstrating specificity of the CAR for certain, but not all HLA molecules.

Example 2: HLA-A2 Specific Regulatory T Cells

Figure 4:
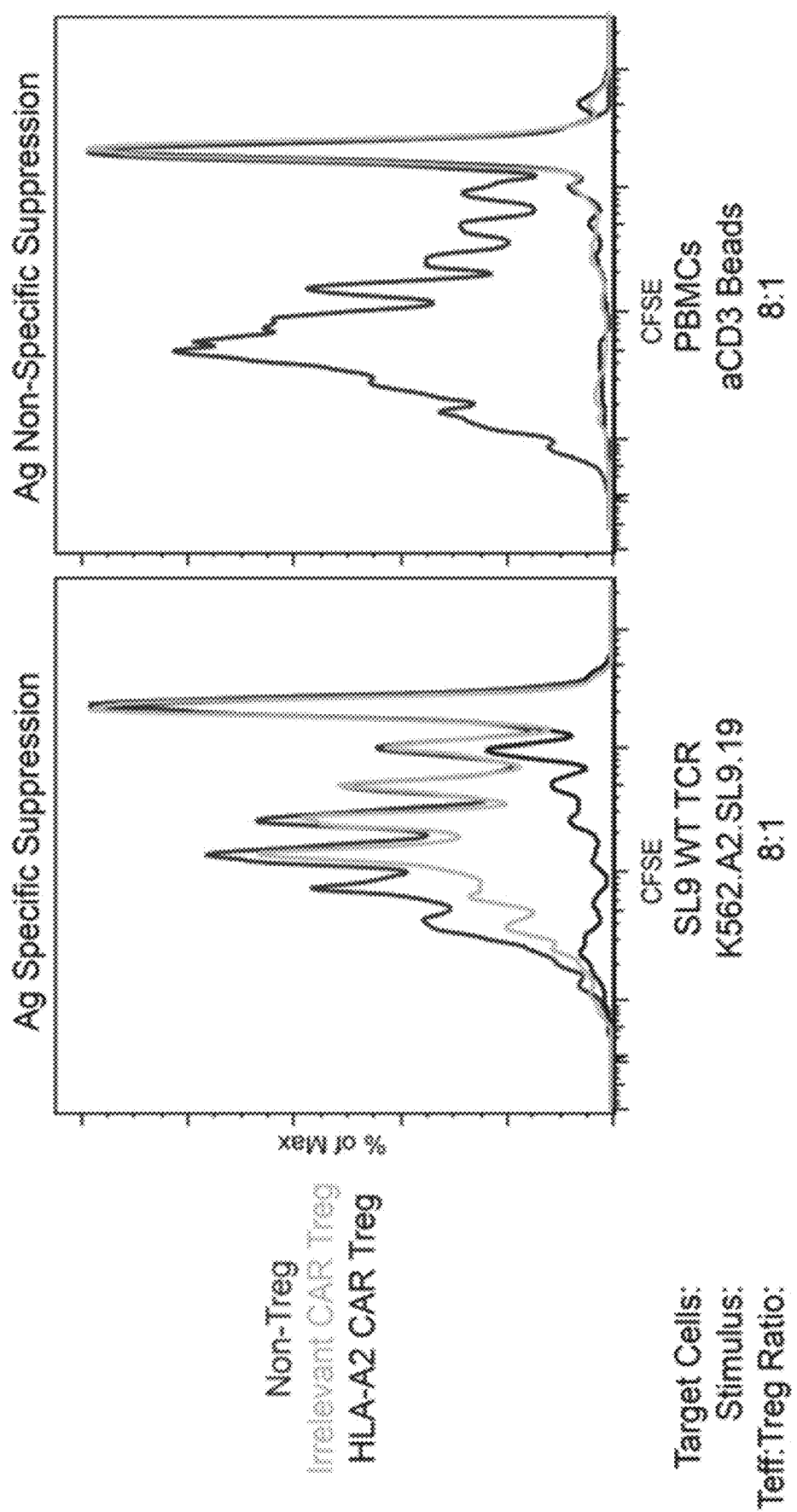
FIG. 4 is a pair of plots illustrating regulatory T cells isolated from human cord blood donors via CD4+ RosetteSep followed by CD25 positive magnetic selection. Tregs were stimulated with α-CD3/α-CD28 beads and grown in XVIVO15 with κ% human AB serum containing 1× GlutaMAX and 300 IU/mL IL-2. Forty-eight hours following initial stimulation, the Tregs were lentivirally transduced to express 3PF12-28z CAR or an irrelevant CAR. When cells were rested down at day 14, antigen specific suppression was assayed by mixing Tregs with CFSE labeled, allogeneic T cells expressing the A2-SL9 WT TCR (an HIV-specific TCR) and K562 cells which transgenically express HLA-A2 at a ratio of 8:1:0.5 (Teff:Treg:K562). To probe non-specific suppressor function, Tregs were mixed with CFSE labeled, allogeneic PBMCs and α-CD3 stimulator beads at a ratio of 8:1:3 (Teff:Treg:Beads). CFSE dilution was measured among CD8+ T cells after 5 days of cell culture.

Regulatory T cells were isolated from human cord blood donors via incubation with CD4+ RosetteSep reagent (Stem Cell), layering over Lymphoprep, and 30 minute centrifugation at 400×g for 30 minutes, followed by CD25 positive magnetic selection (StemCell Technologies). Tregs were stimulated with α-CD3/α-CD28 beads (Gibco) and grown in XVIVO15 with 5% human AB serum (Invitrogen) containing 1× GlutaMAX and 300 IU/mL IL-2 and placed in a 37° C./5% $CO_2$ incubator. Forty-eight hours following initial stimulation, the Tregs were lentivirally transduced to express 3PF12-28z CAR or an irrelevant CAR. α-CD3/α-CD28 beads were removed on day 4, and the cells were fed the above complete XVIVO15 medium on days 4, 6, 9, and 12, with IL-2 replaced as needed assuming consumption. When cells rested down at day 14, antigen specific suppression was assayed by washing the Tregs three times to remove IL-2, and mixing them with allogeneic T cells that had been electroporated with RNA to express the SL9 WT TCR and labeled with 2.5 µM CFSE sixteen hours prior, and K562 cells which transgenically express HLA-A2 and SL9 antigen at a ratio of 8:1:0.5 (Teff:Treg:K562). To probe non-specific suppressor function, Tregs were mixed with CFSE labeled, PBMCs and α-CD3 stimulator beads (Gibco) at a ratio of 8:1:3 (Teff:Treg:Beads). After 5 days of incubation in a 37° C./5% $CO_2$ incubator, cells were stained with 1 µL CD8-APC-H7 and 0.5 µL CD4-BV421 antibodies diluted in 100 µL PBS for 15 minutes at 4° C. before being washed and resuspended in 2% PFA for fixation. Cells were then analyzed on a LSR II flow cytometer (FIG. 4). Without any other intervention, the CFSE labeled target cells will divide due to the interaction of SL9 WT TCR and the SL9 peptide presented by MHC Class I expressed on the K562 cells, resulting in a dilution of CFSE signal. Cell division was suppressed by co-culturing HLA-A2+ CAR Tregs with the target cells, as evidenced by less dilution of CFSE signal (blue). In contrast, the CFSE target cells were highly proliferative when co-cultured with either irrelevant CAR Tregs (green) or non-Treg CD4+ T cells (red). To show that both sets of Tregs had equal suppressive potential, the right panel of FIG. 4 shows that upon polyclonal stimulation of CFSE labeled PBMCs and Tregs in co-culture by α-CD3 stimulator beads, both irrelevant (green) and HLA-A2+(blue) CAR Tregs suppress equally, at a level much higher than non-Treg CD4+ cells (red).

Example 3: HLA-A2 Specific T Cells Target HLA-A2+ Islets

Figure 5:
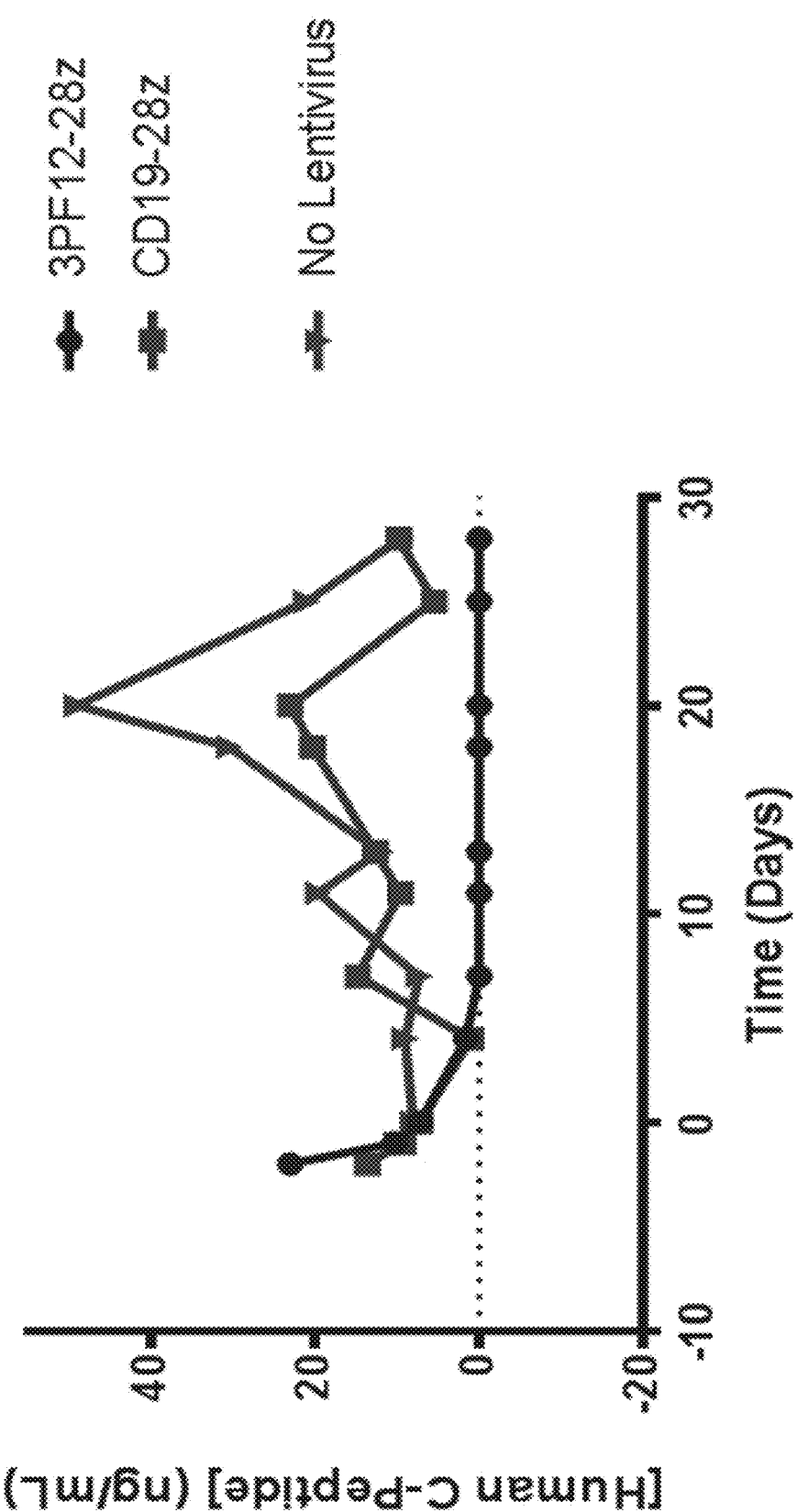
FIG. 5 depicts human C-peptide levels in response to 3PF12-28z or CD19-28z CAR transduced T cells, or untransduced negative control T cells.

HLA-A2+ islets from human donors were transplanted under the left kidney capsule of NSG mice. Three days later, $10 \times 10^6$ lentivirally transduced T cells bearing either 3PF12-28z or irrelevant CD19-28z CARs were injected intravenously. Untransduced T cells were used as a negative control. Urine samples were collected periodically and banked at −80 C until they were assessed for human c-peptide levels by ELISA (FIG. 5). As shown in FIG. 5, 3PF12-28z CAR transduced T cells were capable of depleting human C-peptide levels, indicating that the 3PF12-28z CAR transduced T cells targeted the transplanted HLA-A2+ islets.

Example 4: HLA-A2 Specific Tree Adoptive Immunotherapy for Treatment of Type 1 Diabetes Type 1 diabetes is a T cell-mediated autoimmune disease resulting in islet beta-cell destruction, hypoinsulinemia, and severely altered glucose homeostasis. Failure of regulatory T cells (Tregs) may play a role in the development of type 1 diabetes. During immune homeostasis, Tregs counterbalance the actions of autoreactive effector T cells, thereby participating in peripheral tolerance. Thus, an imbalance between effector T cells and Tregs may contribute to the breakdown of peripheral tolerance, leading to the development of type 1 diabetes.

Autologous Tregs are isolated from a subject and stimulated and expanded ex vivo. Tregs are lentivirally transduced with an HLA-A2 CAR to produce HLA-A2 specific Tregs. HLA-A2 specific Tregs, e.g., those produced in Example 2 (3PF12-28z CAR transduced Tregs), will be administered to a subject having type 1 diabetes.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A modified immune cell or precursor cell thereof, comprising a chimeric antigen receptor (CAR) having affinity for HLA-A2, wherein the CAR comprises, from N-terminus to C-terminus, a CD8 signal peptide, a HLA-A2 scFv binding domain comprising the amino acid sequence set forth in SEQ ID NO: 1, a CD8 hinge domain, a CD28 transmembrane domain, a CD28 intracellular domain, and a CD3 zeta intracellular domain, and wherein the HLA-A2 scFv binding domain cross-reacts with HLA-A28.

2. The modified immune cell or precursor cell thereof of claim 1, wherein the modified cell is a modified regulatory T cell.

3. The modified immune cell or precursor cell thereof of claim 1, wherein the modified cell is an autologous cell derived from a human.

4. An isolated nucleic acid comprising a nucleic acid sequence encoding a chimeric antigen receptor (CAR) having affinity for HLA-A2, wherein the CAR comprises, from N-terminus to C-terminus, a CD8 signal peptide, an HLA-A2 binding domain comprising the amino acid sequence set forth in SEQ ID NO: 1, a CD8 hinge domain, a CD28 transmembrane domain, a CD28 intracellular domain, and a CD3 zeta intracellular domain.

5. The isolated nucleic acid of claim 4, wherein the nucleic acid sequence comprises the sequence set forth in SEQ ID NO: 24.

6. An expression construct comprising the isolated nucleic acid of claim 4.

7. The expression construct of claim 6, wherein the expression construct comprises an EF-1α promoter, a rev response element (RRE), a woodchuck hepatitis virus post-transcriptional regulatory element (WPRE), and a cPPT sequence, and wherein the expression construct is a viral vector selected from the group consisting of a retroviral vector, a lentiviral vector, an adenoviral vector, and an adeno-associated viral vector.

8. The modified immune cell or precursor cell thereof of claim 1, wherein the CD8 signal peptide comprises the amino acid sequence set forth in SEQ ID NO: 13.

9. The modified immune cell or precursor cell thereof of claim 1, wherein the CD8 hinge domain comprises the amino acid sequence set forth in SEQ ID NO: 15.

10. The modified immune cell or precursor cell thereof of claim 1, wherein the CD28 transmembrane domain comprises the amino acid sequence set forth in SEQ ID NO: 17.

11. The modified immune cell or precursor cell thereof of claim 1, wherein the CD28 intracellular domain comprises the amino acid sequence set forth in SEQ ID NO: 19.

12. The modified immune cell or precursor cell thereof of claim 1, wherein the CD3 zeta intracellular domain comprises the amino acid sequence set forth in SEQ ID NO: 21.

13. The modified immune cell or precursor cell thereof of claim 1, wherein the CAR comprises the amino acid sequence set forth in SEQ ID NO: 23.

* * * * *